(12) United States Patent
Cheng

(10) Patent No.: US 9,770,415 B2
(45) Date of Patent: Sep. 26, 2017

(54) DELIVERY SUBSTRATES FROM ALIGNED POLYMER BIOMATERIALS FOR TISSUE REPAIR

(71) Applicant: Southwest Research Institute, San Antonio, TX (US)

(72) Inventor: Xingguo Cheng, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 14/075,564

(22) Filed: Nov. 8, 2013

(65) Prior Publication Data

US 2014/0147494 A1 May 29, 2014

Related U.S. Application Data

(60) Provisional application No. 61/730,261, filed on Nov. 27, 2012.

(51) Int. Cl.
*A61K 9/127* (2006.01)
*A61K 38/39* (2006.01)
*A61K 38/18* (2006.01)
*A61K 9/51* (2006.01)

(52) U.S. Cl.
CPC .......... *A61K 9/127* (2013.01); *A61K 38/1858* (2013.01); *A61K 38/39* (2013.01); *A61K 9/1271* (2013.01); *A61K 9/5153* (2013.01)

(58) Field of Classification Search
None
See application file for complete search history.

(56) References Cited

U.S. PATENT DOCUMENTS

| | | | |
|---|---|---|---|
| 4,944,948 A * | 7/1990 | Uster et al. | 424/450 |
| 5,270,300 A * | 12/1993 | Hunziker | 514/13.3 |
| 6,544,549 B1 * | 4/2003 | Boni et al. | 424/450 |
| 8,557,956 B2 | 10/2013 | Cheng et al. | |
| 2005/0033362 A1 * | 2/2005 | Grafton | 606/228 |
| 2008/0160060 A1 * | 7/2008 | Ellies | 424/422 |
| 2010/0174368 A1 | 7/2010 | Lynch et al. | |
| 2010/0311949 A1 * | 12/2010 | Akkus et al. | 530/356 |
| 2011/0306754 A1 * | 12/2011 | Cheng | C25B 7/00 530/356 |

FOREIGN PATENT DOCUMENTS

WO  2009073548 A1  6/2009

OTHER PUBLICATIONS

Cheng, X, et al "An Electrochemical Fabrication Process for the Assembly of Anisotropically Oriented Collagen Bundles", Elsevier, Biomaterials 29, 2008, pp. 3278-3288.
Cheng, X, et al, "Electrochemical Bioencapsulation of Nanomaterials Into Collagen for Biomedical Applications", Science Research, Journal of Encapsulation and Adsorption Sciences, 2013, 3, pp. 16-23.
Jin, Q, et al, "Nanofibrous Scaffolds Incorporating PDGF-BB Microspheres Induce Chemokine Expression and Tissue Neogenesis In Vivo", PLOSone, www.plosone.org, PDGF Nanoscaffolds for Repair, Mar. 2008, vol. 3, Issue 3, e1729.
Wei, G, et al, Nano-fibrous Scaffold for Controlled Delivery of Recombinant Human PDGF-BB, Elsevier, Science Direct, Journal of Controlled Release 112 (2006), pp. 103-110.

* cited by examiner

*Primary Examiner* — Brian Gulledge
(74) *Attorney, Agent, or Firm* — Grossman, Tucker et al.

(57) ABSTRACT

An aligned polymer article including substrates, wherein the substrates are not covalently bonded to the aligned collagen and a method of forming such articles wherein substrates are mixed with a polymer in solution to form a polymer-substrate mixture. The mixture is placed in an electrochemical cell and a voltage is applied to the cell generating a pH gradient, wherein the polymer aligns in the cell and migrates to the isoelectric plane of the polymer solution.

18 Claims, 25 Drawing Sheets

DELIVERY SUBSTRATES FROM ALIGNED POLYMER BIOMATERIALS FOR TISSUE REPAIR

CROSS REFERENCE TO RELATED APPLICATIONS

The present application claims the benefit of the filing date of U.S. provisional application Ser. No. 61/730,261, filed Nov. 27, 2012, the teachings of which are incorporated herein by reference.

GOVERNMENT SUPPORT CLAUSE

This invention was made with United States Government support under Contract No. W81XWH-10-1-0986 from the United States Army. The Government has certain rights in this invention.

FIELD OF INVENTION

The present disclosure relates to a method for forming aligned polymer containing substrates for tissue repair, via electrochemical procedures, without covalent bonding of the substrates to the polymer.

BACKGROUND

Optimal characteristics of tissue graft material, including synthetic graft material, includes good biomechanical properties, biodegradability and cell-supporting properties. Collagen has been examined as it is both biodegradable, biocompatible and the primary component of extracellular matrices (ECM) of tendons/ligaments, skin and the organic component of bone. However, traditional FDA-approved collagen-based grafts have relatively weak biomechanical properties and generally lack the ability to control delivery of certain growth factors. Accordingly, advances in synthetic tissue graft material, and particularly in improving the biomechanical properties of collagen graft material, is desirable and remains of interest.

SUMMARY

An aspect of the present disclosure relates to forming an aligned polymer containing substrates. The method includes mixing a polymer in solution and substrates to form a polymer-substrate mixture. The method also includes placing the mixture in an electrochemical cell contacting the mixture with two electrodes. The method further includes applying a voltage to the electrochemical cell and generating a pH gradient wherein the polymer aligns in the cell and migrates to the isoelectric plane of the polymer in solution. In addition, the method includes forming an aligned polymer article including the substrates without covalently bonding the substrates and the polymer.

Another aspect of the present disclosure relates to a method of stimulating adipose derived stem cell proliferation. The method includes seeding aligned collagen including nanoparticles encapsulating platelet derived growth factor with adipose derived stem cells and incubating the cells for at least 24 hours.

A further aspect of the present disclosure relates to a method of stimulating human gingival cell proliferation. The method includes seeding aligned collagen including nanoparticles encapsulating platelet derived growth factor with human gingival cells and incubating the cells for at least 24 hours.

Yet another aspect of the present disclosure relates to an article comprising a composition of aligned collagen including nanoparticles encapsulating a pharmaceutical composition, wherein the nanoparticles are not covalently bonded to the aligned collagen.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
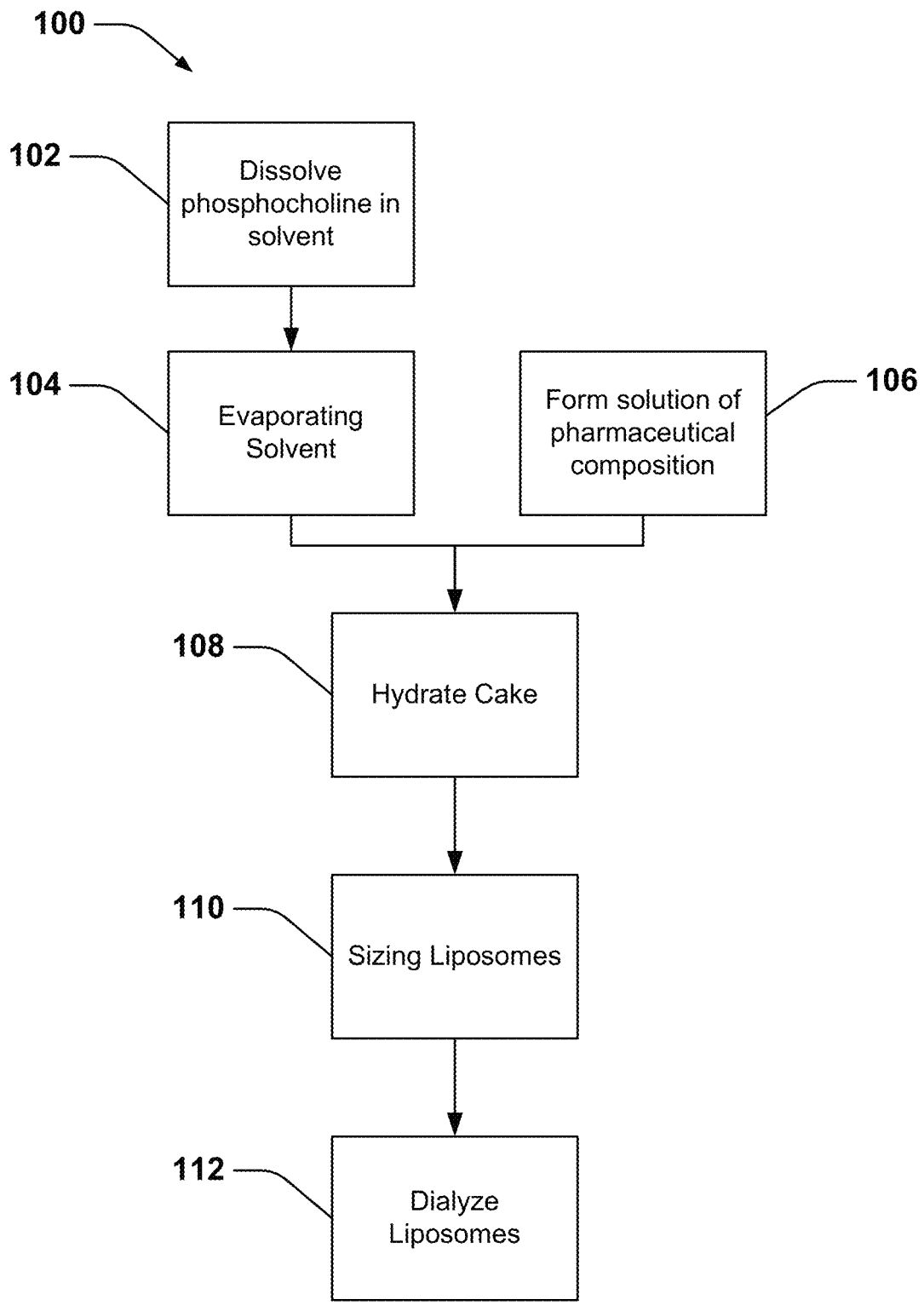
FIG. 1 is a flow chart of a method for making lipo some nanoparticles.

It may be appreciated that the present disclosure is not limited in its application to the details of construction and the arrangement of components set forth in the following description or illustrated in the drawings. The embodiments herein may be capable of other embodiments and of being practiced or of being carried out in various ways. Also, it may be appreciated that the phraseology and terminology used herein is for the purpose of description and should not be regarded as limiting as such may be understood by one of skill in the art.

As noted above, the present disclosure is directed to articles including substrates, such as nanoparticles including a pharmaceutical composition, loaded into an aligned polymer biomaterial. The articles may be used for various treatments in the repair or regeneration of flesh and connective tissue in subjects. The aligned polymer biomaterials may be formed as described in U.S. application Ser. No. 12/813,834, entitled "Aligned Polymers Including Bonded Substrates", filed on Jun. 11, 2010, published on Dec. 15, 2011, as U.S. Publ. No. 2011/0306754, the teachings of which are incorporated herein by reference. However, the present disclosure recognizes that the substrates may be loaded into the aligned polymer biomaterials without covalent bonding. The benefits of not having to covalently bond the substrates to the aligned polymers include removal of the need to place chemical functional groups on the substrate and polymer which would otherwise lead to covalent bonding attachment.

A "pharmaceutical composition" is understood herein as a compound that exhibits biological activity, including nutritional, nutraceutical and/or pharmacological activity, which may be used in identification, diagnosis or treatment of a pathology or disease. A "pharmaceutical composition" also includes those compounds used in analysis to identify, diagnose or treat a condition such as dyes, stains, markers, labels, or indicators. As used herein the term "treatment" or "treat" refers to administrating to an individual an effective amount of a pharmaceutical composition which, alleviates, slows the progression of, speeds the healing of, improves the healing response of, prevents additional symptoms of, repairs a pathology for which the individual is being treated and/or which results in one or more desirable clinical or therapeutic effects which include, but are not limited to, alleviation of pain, increase in range of motion, increase in strength and attachment of or associated to a tendon, ligament, skin, bone, or nerve. Thus the term may denote that a beneficial result has been conferred on a vertebrate subject. An "effective amount" refers to that amount effective to achieve or produce an observable result, which in the present application includes, for example, an increase in the proliferation of adipose-derived stem cells or human gingival cells as described further herein.

Biomaterial is understood as a material that is either biodegradable, biocompatible or both. Biodegradable is understood as the ability of being broken down by enzymatic processes produced by living organisms such as by biological agents including, for example, bacteria, enzymes, cells, etc. Biocompatible is understood as encompassing those materials capable of performing an appropriate response in a subject in a specific application and, more particularly perform such a function with minimal detriment to surrounding tissue.

The polymer alignment noted herein may be preferably achieved according to electrochemical methods and reference is made to WO2009/073548. More generally, the alignment may be achieved by providing an aqueous (e.g. distilled water) solution of polymer capable of alignment (e.g. a protein such as collagen), placing the solution into an electrochemical cell wherein the solution is in contact with two electrodes, applying an electric field wherein the current density is 0.3 A/m$^2$ to about 34 A/m$^2$ and generating a pH gradient in the solution, wherein the polymer positions at the isoelectric point of the polymer in the solution. The isoelectric point (pI), sometimes abbreviated to IEP, is the pH at which a particular polymer carries no net electrical charge. The amount of polymer in the solution may be in the range of 0.5 mg/ml to 20 mg/ml, the electric field strength may be 100 V/m to 30 KV/m, and the voltage applied to the electrochemical cell may be at least 1.2 V. In embodiments, the electrodes may be tubular, the electrodes may include two linear electrodes, the electrodes may include parallel line electrodes, the electrodes may be in the form of rings, the electrodes may be in the form of plates, etc. The electrodes may be formed from carbon, stainless steel, gold plated metals, magnesium alloy, platinum, any other conductive compositions or combinations thereof.

An apparatus for aligning polymer molecules including substrates is also disclosed herein, and may include a first electrode and a second electrode each in contact with a substrate, the first electrode and second electrode having a gap therebetween configured to receive the polymer solution, a moisture chamber having the substrate, the first electrode and the second electrode position therein, and a power supply electrically connected to the first electrode, the power supply configured to supply a voltage to the first electrode and the second electrode to create an electric field in the gap such that each polymer molecule received in the gap is aligned along its respective isoelectric point.

The apparatus may further include a resistive element connected to the power supply and one of the first and second electrodes, the substrate may be formed of glass, plastic, ceramic, metal or combinations thereof, the power supply may be a dc or ac power supply, the first electrode and second electrode may comprise a wire or plate or tube, the first electrode may be tubular and the second electrode may be positioned within the first electrode and extend along the longitudinal axis of the first electrode, the first electrode may comprise a loops and the second electrode may be positioned within such loop, the first and second electrodes may be formed from materials selected from the group consisting of carbon, stainless steel, gold, gold plated metals and platinum or any other conductive electrodes.

The method for alignment of the polymer molecules containing substrates may include dispensing the polymer molecules with substrates in a gap between a first and second electrode, applying a voltage to the electrodes to produce an electric field in the gap and controlling the voltage applied to the electrodes to align each polymer molecule along their respective isoelectric point.

As therefore alluded to above, the polymers capable of alignment herein include those polymers that may be aligned in the electric field at the polymer isoelectric point. Such polymers may therefore preferably include those polymers capable of assuming a defined polarity and then orientating with respect to an anode or cathode electrode. Such polarity preferably includes the development of a net positive and/or negative charge, such that the polymer may then align, as noted herein, at their respective isoelectric point. Preferably, such polymers may include polypeptides and proteins and more specifically collagen, and for the purpose of this disclosure, collagen has been utilized to demonstrate the general characteristics of alignment of the herein described polymers now containing a substrate. However, while collagen is preferably utilized it can be readily appreciated that the present disclosure extends to polymers which when in aqueous solution may be exposed to an electric field and pH adjustment and undergo alignment and which alignment may then be imposed upon any selected bound substrate.

The pH for electrochemical alignment may be selected from a range of 3.0 to 11.0, and more preferably, at a range of 6.0 to 9.0. In certain embodiments the pH range may preferably be in the range of 7.0 to 8.5, and more particularly, at a level of 7.3 to 7.4. The polymer in the aqueous solution within the electrochemical cell may be present at a concentration of 0.1 mg/ml to 10 mg/ml or higher. The aligned polymers of the present disclosure may indicate modulus values of 50 MPa to 1.5 GPa, including all values and increments therein in 100 MPa increments. Modulus may be understood as reference to the elastic modulus and the slope of the stress versus strain curve in mechanical testing. The tensile stress may be in the range of 0.5 MPa to 150 MPa, also in 100 MPa increments. Tensile strain values may vary between 0.05% to 30%. The density of the aligned polymer systems may be from around 1.0 g/mL to 3.0 g/mL.

With respect to the reference to collagen herein, such may be generally understood as a group of naturally occurring proteins found in connective tissue of animals, and containing three polypeptide chains in the form of a triple helix. The amino acid sequence in collagen typically follows the sequence Gly-Pro-X or Gly-X-Hyp where Gly refers to glycine, Pro refers to proline or hydroxyproline and X may be any of the various amino acid residues. The collagen herein may therefore be any type of collagen including collagen types I to XXVII, alone or in combination, or even collagen-mimic peptide. The collagen may contain endogenous or exogenously added non-collagen proteins (e.g. fibronectin, fibrinogen, keratin or silk proteins), glycoproteins, proteoglycans, polysaccharides, glycosaminoglycans (e.g. chondroitins and heparins).

The substrates may now be loaded into the aligned polymer molecules without covalent bonding, i.e., the sharing of electrons as between atoms of the substrate and the aligned polymer. Accordingly, other forms of bonding, such as polar interactions, may be established as between the substrates and the aligned polymers. Polar interactions are understood to include van der Waals forces and/or dipole-dipole forces. The substrates include any chemical compound and/or specific structures, such as nanoparticles, nanotubes or both. The substrates may also include nanowires, nanobelts, nanoribbons, nanorods or combinations thereof. The chemical compounds may preferably include polypeptides (synthetic or natural) and/or proteins.

Nanoparticles may be understood herein as any particle exhibiting a mean particle size in the range of 1 nm to 3,000 nm, and preferably 1 nm to 999 nm, and more preferably, 1 nm to 300 nm. The nanoparticles and/or nanotubes herein may themselves be bonded to or associated with a pharmaceutically active ingredient (PAI), such as a pharmaceutical composition for targeted drug delivery. The level of nanoparticle and/or nanotube loaded into the aligned polymers herein may preferably be present in an amount of 25 wt. % or higher. However, the level of nanoparticles and/or nanotubes loaded into the aligned polymers may be in the range of 0.01 wt. % to 99 wt. %, and at all values therein, in 1.0 wt % increments. Preferred examples of substrates for use herein include nanoparticles of liposomes including phosphocholine liposomes, biodegradable polyester based nanoparticles such as PLGA-based nanoparticles, inorganic nanoparticles such as silver and gold, calcium phosphate-based particles, and any non-PH sensitive nanoparticle or nanomaterial as well as various dyes.

Nanotubes herein may be understood as any tubular type structure that has nanometer dimensions in the range of 1-999 nm, and more typically 1-100 nm. Such may therefore include, e.g., carbon nanotubes (CNT), inorganic nanotubes (e.g. metal oxides), DNA nanotubes and/or membrane nanotubes (a tubular membrane connection between cells).

Accordingly, while the substrates may include any one or more of the above referenced nano-type structures, for exemplary purposes only, the present disclosure identifies a representative nanoparticle-collagen systems, and it is again to be understood than any substrate loaded into the electrochemically alignable polymers, without the necessity of covalent bonding, may be employed.

In embodiments, forming the substrate loaded aligned polymer optionally begins by obtaining or fabricating nanoparticles including a pharmaceutical composition such as a growth factor including platelet derived growth factor (PDGF), bovine serum albumin (BSA), a dye or combinations thereof. In embodiments, the nanoparticles are not easily dissolvable in highly acidic, i.e., pH≤2 or highly basic, i.e., pH≥12, conditions. The nanoparticles or nanomaterials may be formed by, for example, liposome encapsulation techniques and emulsion techniques including water in oil in water emulsion techniques.

FIG. 1 illustrates a method 100 of forming nanoparticles encapsulating a pharmaceutical composition using liposome encapsulation techniques. The method includes dissolving phosphocholine, such as 1,2-distearoyl-sn-glycero-3-phosphocholine (DSPC) or 1,2-dimyristoyl-sn-glycero-3-phosphocholine (DMPC), in a solvent 102. The solvent may include non-polar solvents such as chloroform or chloroform/methanol mixtures. Optionally added are a phospholipid PEG conjugate and a fluorescent phospholipid for tracking concentration. Furthermore, the phospholipid PEG conjugate includes, for example, DSPE-PEG-amine. The fluorescent phospholipid includes, for example, HPC-DPH.

The solvent is then evaporated 104 to provide a cake, or dried film of lipids, under a stream of inert gas, such as nitrogen. Separately, a pharmaceutical composition in solution is prepared 106. The pharmaceutical composition includes, for example, platelet derived growth factor (PDGF), bovine serum albumin (BSA) or dye formulation such as fluorescent phospholipids. In addition, solvents may include, for example, water. In preferred embodiments a platelet derived growth factor solution is utilized wherein the concentration of the solution is in the range of 25 µg/mL to 2 mg/mL, including all values and ranges therein, such as 50 µg/mL to 1 mg/mL. In additional preferred embodiments, a bovine serum albumin solution is utilized wherein the concentration of the solution is in the range of 1 mg/mL to 20 mg/mL, including all values and ranges therein, such as 10 mg/mL. From 10 µL to 500 µL of water is optionally added, including all values and ranges therein, such as in the range of 50 µL to 300 µL. Alternatively, or in addition to, water, other solvents may be used such as buffered solutions, saline and nonelectrolyte solutions are added to the platelet derived growth factor solution.

The dried cake is then hydrated 108 with the pharmaceutical solution. The lipids form liposomes, such as multilayered vesicles, in the solution. The liposomes are sized 110 using mechanical methods, such as extrusion or sonication. In embodiments, the liposomes are extruded from 5 to 20 times, including all values and ranges therein, such as 10 times, through a membrane having a pore size in the range of 0.1 µm to 0.5 µm, including all values and ranges therein, such as 0.2 µm. The liposomes are then dialyzed 112 to remove un-encapsulated pharmaceutical compositions. Dialysis tubing may be used wherein the molecular weight cut-off is in the range of 10,000 to 200,000, including all values and ranges therein.

The effective diameter of the liposomes is in the range of 100 nm to 300 nm, including all values and ranges therein, such as 130 nm to 220 nm, 130 nm to 170 nm, 200 nm to 220 nm, etc. Furthermore, the liposomes may exhibit a polydispersity in the range of 0.050 to 0.300, including all values and ranges therein such as 0.050 to 0.250, 0.100 to 0.230, etc. In addition, the loading efficiency of the liposomes is in the range of 75 to 95%, including all values and ranges therein, and preferably 85% to 95% and more preferably 90%. Loading efficiency as understood herein is determined by a Lowry protein assay and enzyme-linked immunosorbent assay (ELISA).

Figure 2:
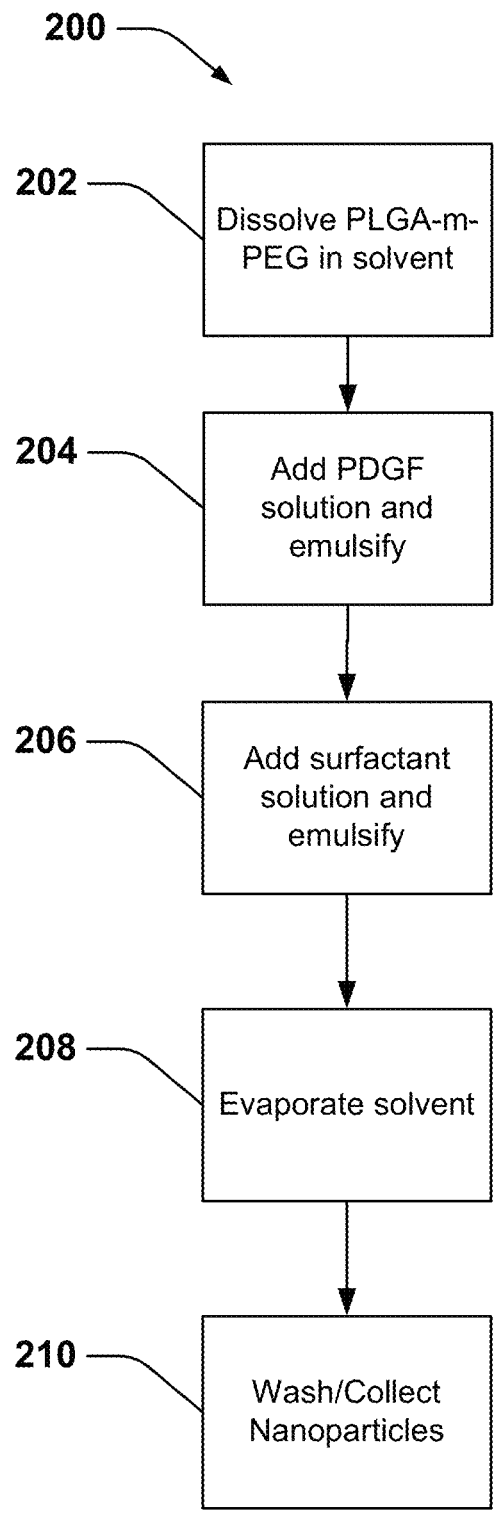
FIG. 2 is a flow chart of a method for making PLGA-m-PEG nanoparticles.

As alluded to above, the nanoparticles for encapsulating a pharmaceutical based composition can alternatively be formed using water-oil-water double emulsion technique, an embodiment of which is illustrated in FIG. 2. In this method 200 poly(lactic-co-glycolic acid)-monomethoxy-poly(ethylene glycol) (PLGA-m-PEG) is dissolved in a solvent such as dichloromethane 202. The PLGA-m-PEG may be present at a concentration of 200 mg/4 mL. To this solution, a pharmaceutical composition, such as platelet derived growth factor (PDGF) solution, BSA solution or dye-formulation such as Rhodamine 6G fluorescence dye, is added to and emulsified in the PLGA-mPEG composition (i.e., the oil phase) 206. The PDGF solution, prior to addition to the PLGA-m-PEG solution, exhibits a concentration such as 50 µg/mL. The PLGA-m-PEG solution and pharmaceutical composition solution are present at ratios of 4:0.2.

The mixture of the PLGA-m-PEG solution and pharmaceutical composition solution is then emulsified with a solution including a surfactant 206, such as sodium cholate. The surfactant is present in at a concentration such as 1%, in the surfactant solution. After addition, the surfactant solution, PLGA-m-PEG solution, and pharmaceutical composition solution are utilized at ratios such as 40:4:0.2.

Nanoparticles are formed after solvent evaporation 208 at temperatures in the range of −2° C. to 30° C., including all values and ranges therein, such as 0° C. to 20° C., 0° C., 20° C., etc. The nanoparticles are then washed and collected 210. Collection may occur via centrifuge at speeds such as 20,000 rpm for 30 min.

The nanoparticles exhibit an effective diameter in the range of 100 nm to 200 nm, including all values and ranges therein such as 150 nm, etc. In addition, where platelet derived growth factor is the pharmaceutical composition, the PLGA-m-PEG nanoparticles exhibit a loading of 0.1 ng to 10 ng of platelet derived growth factor per mg of PLGA-m-PEG, including all values and ranges therein, such as 0.3 ng to 6.6 ng, 0.3 ng, 6.6 ng, etc.

The nanoparticles described above are loaded into collagen, which is then aligned. Again, this process may be performed without covalent bonding of the nanoparticles with the collagen. During alignment, the collagen may assume a number of geometries, such as fiber or sheet as described further below.

Figure 3:
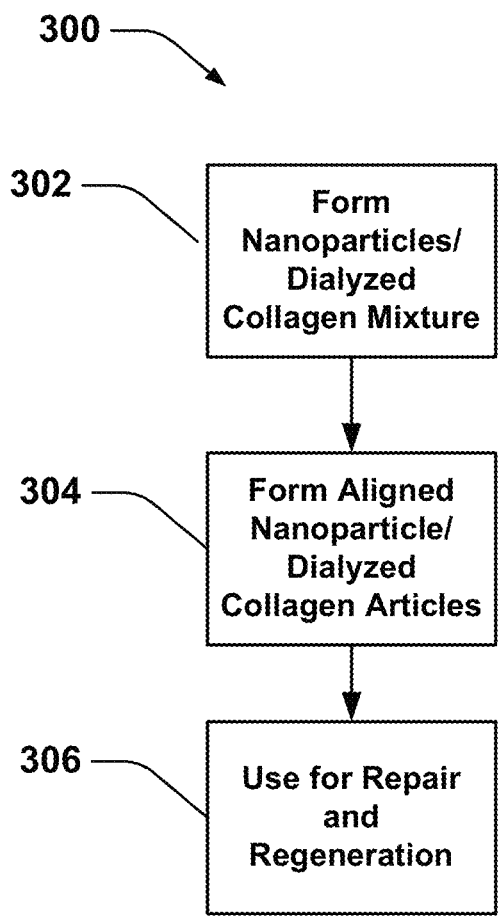
FIG. 3 is a flow chart of a method for forming an aligned collagen—nanoparticle article.

FIG. 3 illustrates an embodiment of a method 300 for loading nanoparticles, and preferably nanoparticles encapsulated with a platelet derived growth factor, into collagen. The method 300 includes mixing the above described nanoparticles with a dialyzed collagen 302. The nanoparticles are provided in a carrier, such as water, at about 3 mg/mL. The collagen is provided in a carrier as well at about 3 mg/mL. The nanoparticle/collagen mixture is then furnished into an electrochemical cell to form fibers 304.

Figure 4A:
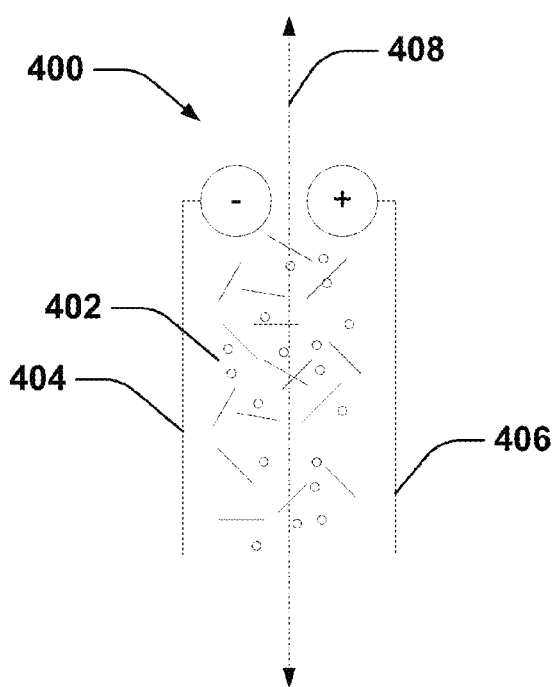
FIGS. 4a and 4b illustrate a schematic of an electrochemical cell.
Figure 4B:
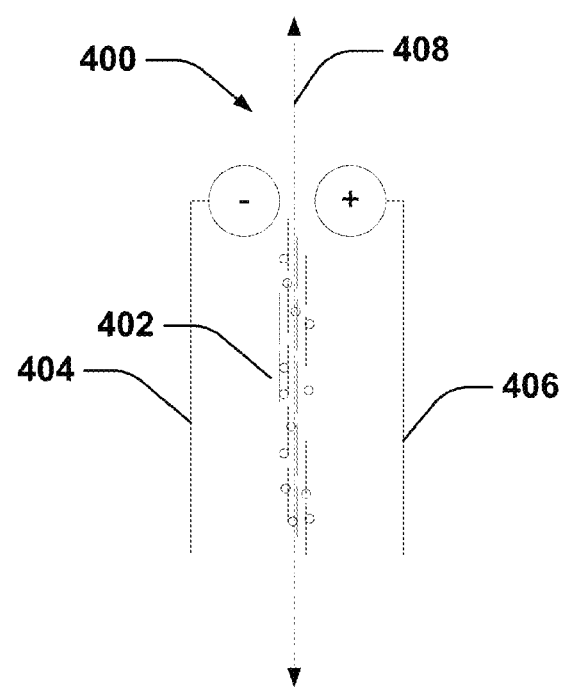

An example of an electrochemical cell is illustrated in FIGS. 4a and 4b. In FIG. 4a the nanoparticle/collagen mixture 402 is furnished into the cell 400, which includes a chamber to hold the mixture. A voltage is applied to the two stationary electrodes, an anode 406 and a cathode 404, forming a pH gradient in the electrochemical cell. To one side of an isoelectric plane 408, in the region proximate to the anode 406, an acidic environment develops and induces a positive charge in the collagen. On the basic side of the isoelectric plane 408, proximate to the cathode 404, a basic environment develops and induces a negative charge in the collagen. The charged polymer molecules then move towards the isoelectric plane, lose their charge and assemble and align into a more solid article. In FIG. 4b, the collagen fibers in the nanoparticle/fiber mixture 402 align, through the development of polarity on the collagen, forming a thread. During the later stages of the electrophoretic process, the thread (or other article being formed) may migrate towards, attach to and provide a coating over the cathode electrode. The voltage applied to the electrochemical cell may be in the range of 1 V to 30 V, including all values and increments therein such as 1 V to 10 V, 3V, etc. The distance between the electrodes is in the range of 0.5 mm to 3 mm, including all values and increments therein, such as 1.5 mm. Referring back to FIG. 3, the fibers may then be used for repair, tissue regeneration or both 306.

Figure 5:
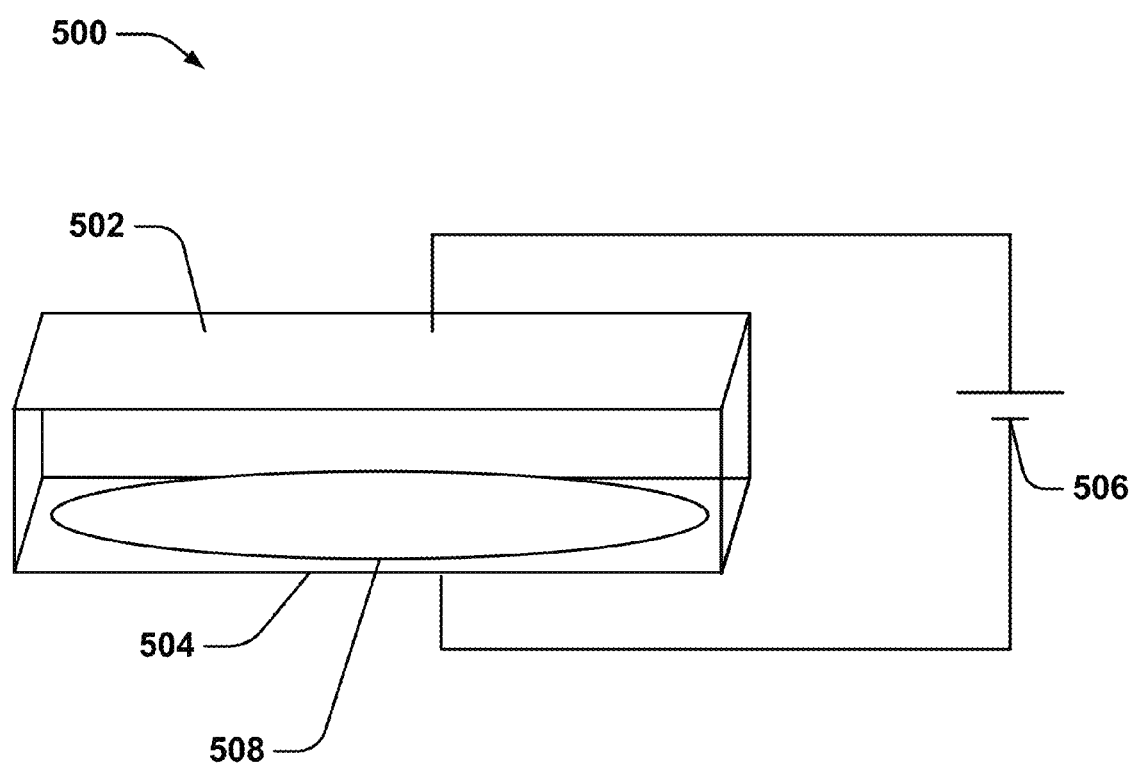
FIG. 5 illustrates a schematic of an electrochemical cell.

In further embodiments, sheets, tubes and other geometries may be fabricated. FIG. 5 illustrates an electrochemical cell for forming a sheet, which includes a plate like anode 502, a plate-like cathode 504 and DC power 506. A nanoparticle-collagen mixture 508 located between the anode and cathode in the cell. The nanoparticle-collagen mixture is isoelectrically focused to the cathode surface within the electrochemical chamber.

Other electrode shapes are suitable for use in the electrochemical cells described herein as well. Examples include circular, wire, plate, ring, tube, etc. Therefore, in addition to the parallel arrangements illustrated in FIGS. 4 and 5, other electrode arrangements may be selected. For example, the electrodes may be cylindrical and arranged concentrically. In the above embodiments, the electrodes, and in particular the cathode, may be patterned, which optionally imparts a pattern on the polymer or is selected to alter the adhesion characteristics of the polymer to the electrodes. The patterns may include microchannels, pores or other configurations to be imparted on the polymer surface.

Figure 6:
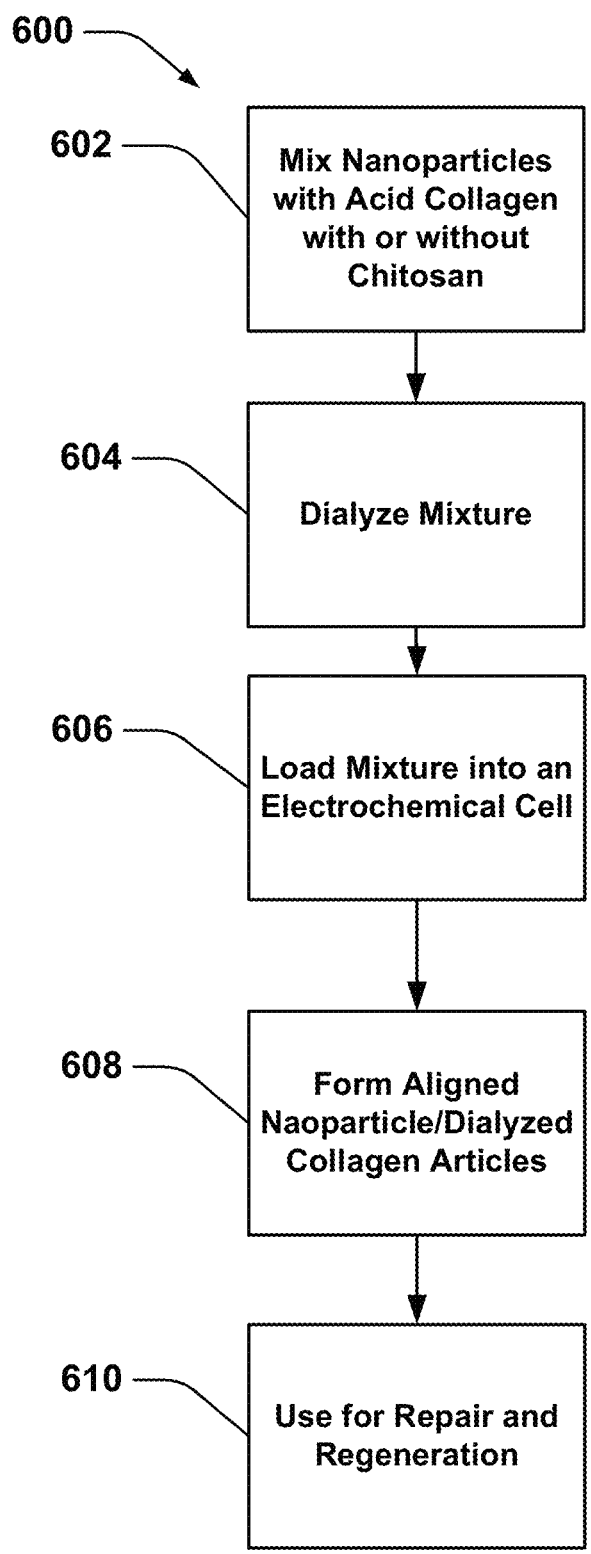
FIG. 6 is a flow chart of a method for forming an aligned collagen-nanoparticle article.

FIG. 6 illustrates an embodiment of another method of loading nanoparticles into collagen. The method 600 includes as illustrated at 602 the mixing of the above described nanoparticles with acid collagen (with or without chitosan). The mixture is dialyzed against ultrapure water 604 or another fluid. The mixture is then loaded into an electrochemical cell 606, such as those described above. A voltage is applied to the cell and articles are formed from the nanoparticle-collagen, such as fibers, sheets or tubes 608. The articles are removed from the electrochemical cell and are used for repair, regeneration or both.

The articles produced herein may assume a variety of shapes including wire, rectangular, square, circular, tubular, ring and combinations thereof. The articles herein exhibit a wall thickness in the range of 100 µm to 2.0 mm. The formed articles may be used as single or double layers, spirally wound, formed into tubes, or folded for various applications. The aligned collagen fibers including said nanoparticles can be braided into a larger structure or different shapes to be used for tendon/ligament or nerve applications. The aligned collagen sheets including said nanoparticles can be used for biomedical application such as tendon/ligament, skin repair and regeneration, etc. The aligned collagen tubes including said nanoparticles can be used as tubular conduits such as vascular grafts, urine and bile conduits, nerve guide tubes, etc. For example, aligned collagen ropes, including the nanoparticles, can be braided into a larger structures or different shapes for use in, for example, tendon/ligament or nerve applications. Aligned collagen sheets including nanoparticles can be used for biomedical application such as tendon/ligament, skin repair and regeneration, etc. Aligned collagen tubes can be used as tubular conduits such as vascular grafts, urine and bile conduits, nerve guide tubes, etc. The articles may be utilized as connective tissue (e.g., tendons, ligaments, endoneurium) or as vascular tissue (e.g., vascular grafts for vascular reinforcement or replacement.)

After 48 hours of digestion at 37° C., which is understood to be a standard for human body temperature, in collagenase (2 mL of 1 mg/mL concentration) digest solution (50 mM TES, 0.36 mM $CaCl_2$, pH 7.4), the nanoparticles release at least 2% of the pharmaceutical composition contained therein and up to 42% of the pharmaceutical composition contained therein. In particular, platelet derived growth factor loaded PLGA-m-PEG nanoparticles in collagen fiber exhibited a 2% release and platelet derived growth factor loaded DMPC liposome nanoparticles in collagen fiber exhibits a 42% release.

The aligned collagen including encapsulated platelet derived growth factor was also found to increase, by at least 40% over a 24 hour period and at least 100% over a 48 hour period adipose-derived stem cell proliferation when compared to pure collagen. In addition, the nanoparticle loaded collagen did not adversely affect the cell viability of the adipose derived stem cells. It was also found that aligned collagen loaded with platelet derived growth factor nanoparticles, as described herein, resulted in a 100% increase in human gingival cell proliferation over pure collagen. Furthermore, it was found that the aligned fibers including the loaded nanoparticles performed better than random fibers including the loaded nanoparticles with respect to tenomodulin, scleraxis and tenascin C gene expression. Specifically, the expression of tenomodulin gene increased by over two fold after a 14 incubation period, scleraxis expression decreased by half and tenascin C gene expression was not significantly changed.

Thus, the present disclosure is directed to stimulating adipose derived stem cell proliferation by seeding aligned collagen including the nanoparticles encapsulating platelet derived growth factor. The cells are then incubated for at least 24 hours, such as from 24 to 48 hours, including all values and ranges therein. This method may be accomplished without detriment to the viability of the stem cells, particularly in comparison to the presence of nanoparticles encapsulating bovine serum albumin.

Similarly, the present disclosure is also directed to stimulating human gingival cell proliferation. The aligned collagen including nanoparticles encapsulating platelet derived growth factor is seeded with human gingival stem cells. The cells are then incubated for at least 24 hours, such as from 24 to 48 hours.

Given the above, and that tissues in the human body are comprised of one or more types of collagen, there are a number of collagen applications in tissue engineering for the herein described nanoparticle loaded collagen material. It is contemplated for example, that the nanoparticle loaded collagen may be used as a tendon repair model. In embodiments, the fibers are braided together to form a functional and developmental scaffold for tears in tendons and ligament tissue. The platelet derived growth factor sustained release promotes the proliferation and differentiation of the stem cells. Further, applications may be found in nerve repair and regeneration.

Further the nanoparticle loaded collagen sheets may be used in dermal repair of large wounds, such as may be necessary in the healing of burns and lacerations. By encapsulating various growth factors, it is contemplated that the wound healing process can be accelerated, leading to better dermal or epidermal regeneration.

Nanoparticle loaded collagen sheets may also be wrapped into tubular membranes forming periosteum sleeves and delivered to periosteum-derived osteogenic factors/cells. The nanoparticle loaded collagen membrane can deliver growth factors or drugs that further enhance bone regeneration. It is contemplated that the tubes may perform better than autogenic periosteum strips.

Another potential application is the development of a scaffold for vascular repair and regeneration, i.e., <3 mm inner diameter. It is contemplated that the nanoparticle loaded collagen solution can be formed into a hollow cylinder shape, which can be used to recreate vasculature with the help of integral cells, such as mesenchymal stem cells and/or angioblasts, and growth factors.

EXAMPLES

Example 1

Fabrication of Liposome-BSA Nanoparticles or Lipo Some PDGF

Preparation Method:

The following outlines a method to fabricate liposome-bovine serum albumin (BSA) or liposome-platelet derived growth factor (PDGF) nanoparticles. Two phosphocholine molecules tested were: (1) 1,2-distearoyl-sn-glycero-3-phosphocholine (DSPC, transition temperature~55° C.) and (2) 1,2-dimyristoyl-sn-glycero-3-phosphocholine (DMPC, transition temperature~23° C.). DSPC Phosphocholine and 1,2-distearoyl-sn-glycero-3-phosphoethanolamine-N-[amino (polyethylene glycol)-2000] (DSPE-PEG-amine) were dissolved in 5 mL of chloroform along with a small amount of HPC-DPH, a fluorescent phospholipid used to track phospholipid concentration. The ratio of phosphocholine:DSPE-PEG-amine:HPC-DPH was 50:1:0.01. For example, a typical DSPC formulation can consist of 79 mg of DSPC and 5 mg of DSPE-PEG-amine. Similar methods were used to fabricate DMPC liposomes. The chloroform was evaporated under a nitrogen gas stream to produce a dried phospholipid film.

Separately, 10 mg/mL of bovine serum albumin (BSA) was dissolved in water. A small volume (50 μL) was added in 10 μL increments to the dried lipid cake in order to hydrate the liposomes and achieve maximal loading efficiency. After BSA had been added, additional water was added to bring the final phospholipid concentration to 10 mM. Liposomes were then extruded 10 times through a 0.2 μm track-etched Nuclepore membrane. After extrusions, liposomes were dialyzed exhaustively in 100,000 Da molecular weight cut-off (MWCO) dialysis tubes to remove unencapsulated BSA. Liposomes were stored at 4° C. until used for additional assays.

The same method as above was used for fabrication of liposomes loaded with platelet derived growth factors (PDGF). A solution (50 μg/mL to 1 mg/mL) of PDGF in water (50 μL to 300 μL) was formed to hydrate the dried lipid cakes of DSPC or DMPC with DSPE-PEG-amine as described above.

Encapsulation Efficiency:

Encapsulation (loading) efficiency of BSA into liposomes was determined by adding equal volumes of liposomes and a solution of 20% sodium dodecyl sulfate (SDS). The liposomes in solution were heated to 60° C. to lyse the liposomes, and then the protein content was determined by a Lowry protein assay (DC Protein Assay, Bio-Rad). Total protein content remaining in the liposomes (encapsulated material) was determined based on a standard curve of known amounts of protein. As determined by protein assay and enzyme-linked immunosorbent assay (ELISA), the loading efficiency of BSA and PDGF inside DMPC liposomes is about 90%.

Figure 7A:
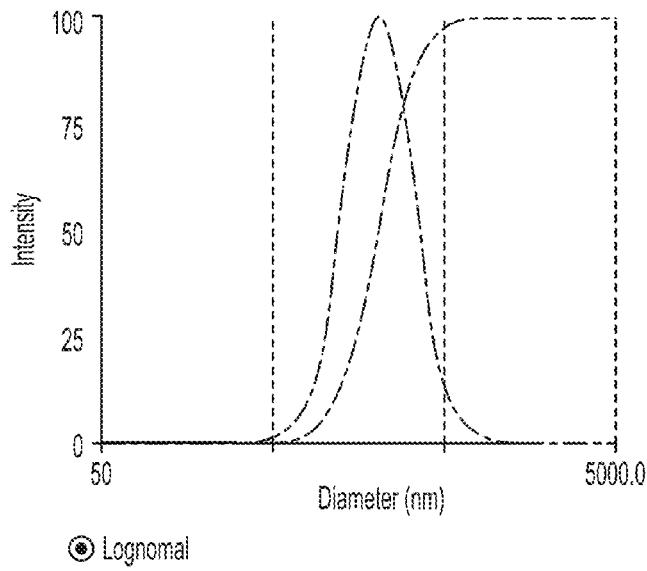
FIG. 7a illustrates an example of an effective diameter analysis for DMPC liposomes.
Figure 7B:
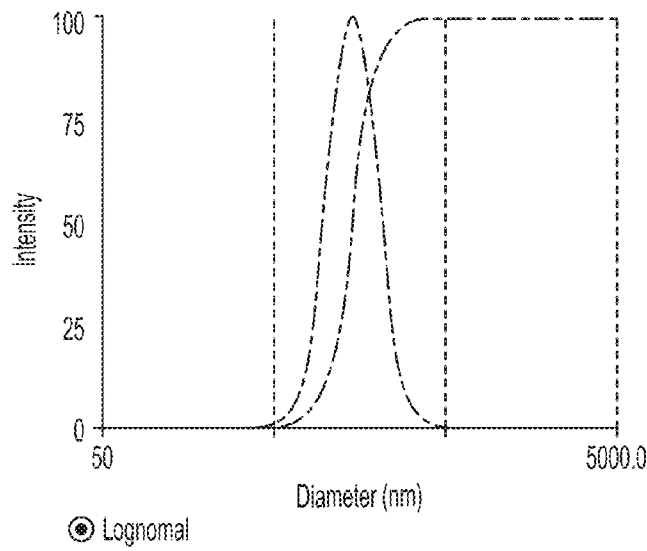
FIG. 7b illustrates an example of an effective diameter analysis for DSPC liposomes.

The effective diameter of the DMPC-PDGF and DSPC-PDGF liposomes was determined. FIG. 7a illustrates the measured particle size distribution for DMPC-PDGF liposomes and FIG. 7b illustrates the measured particle size distribution for DSPC-PDGF liposomes. From these particle size distributions, the effective particle size and polydispersity was determined. For the DMPC-PDGF sample, the effective diameter was found to be 211.6 nm with a polydispersity of 0.230. For the DSPC-PDGF sample, the effective diameter was found to be 146.3 nm with a polydispersity of 0.100.

Example 2

Fabrication of PLGA-m-PEG-PDGF Nanoparticles

Preparation Method:

Poly(lactic-co-glycolic acid)-monomethoxy-poly(ethylene glycol) (PLGA-m-PEG with 5% PEG at 5,000 Dalton, Boehringer Ingelheim, Germany) nanoparticles were fabricated using a water-oil-water double emulsion technique. Briefly, 200 mg of PLGA-m-PEG were dissolved in 4 mL $CH_2Cl_2$ (Sigma), then a PDGF (200 μL 50 μg/mL PDGF) solution was emulsified into the above oil phase. This water-in-oil emulsion was further emulsified in 40 mL of 1% sodium cholate. Nanoparticles are formed after solvent (methylene chloride) evaporation at room temperature or on ice/water bath for three hours. Washed nanoparticles were collected by centrifugation at 20,000 rpm for 30 min.

PDGF Loading:

The washed nanoparticles were lyophilized into a powder for drug loading determination. To quantify the amount of PDGF drug loading, 10 mg of nanoparticles were digested and centrifuged at 10,000 rpm for 15 min. The PDGF concentration in the supernatant was measured by a human PDGF-BB ELISA assay (R&D systems, MN). The typical PDGF loading was determined to be 0.3 ng to 6.6 ng PDGF/mg of PLGA-m-PEG nanoparticles. The loading was dependent on various parameters, e.g., PLGA-m-PEG weight, PDGF solution volume and concentration, sodium cholate volume and concentration, and evaporation condition (e.g., Room temperature vs. 5 degree).

Figure 8:
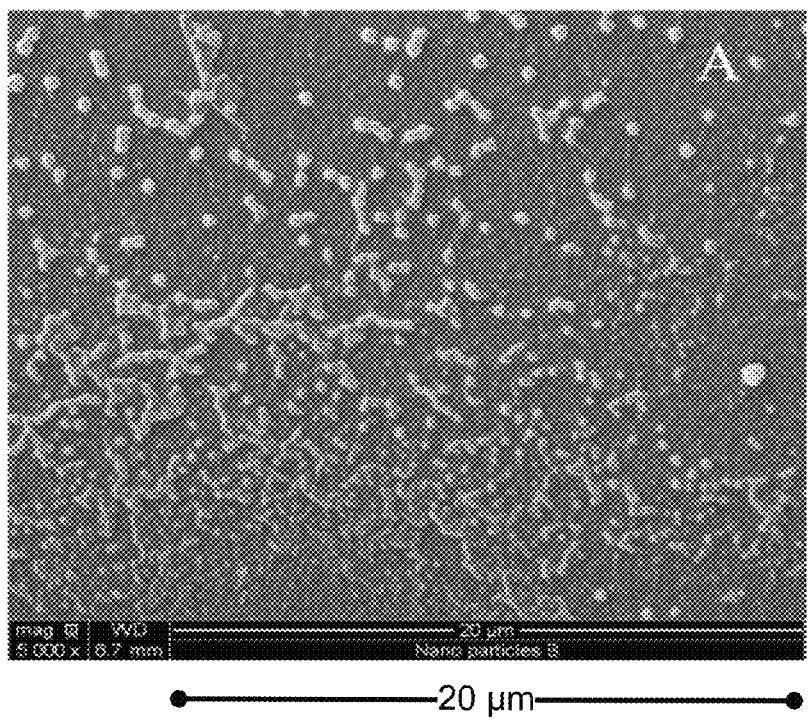
FIG. 8 illustrates a scanning electron microscope image of nanoparticles prepared with PLGA-m-PEG.
Figure 9:
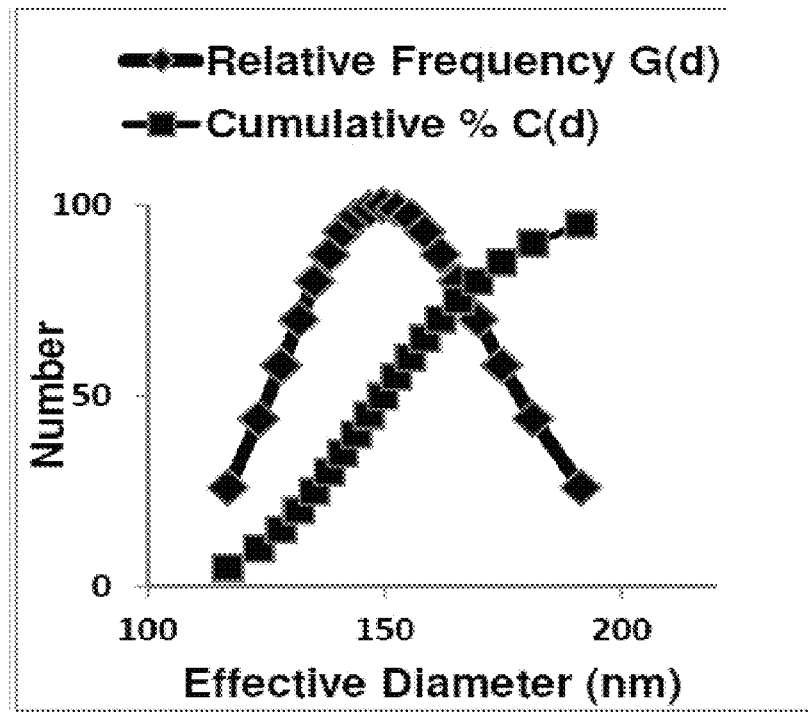
FIG. 9 illustrates an example of the effective diameters of a sample of nanoparticles prepared with PLGA-m-PEG.
Figure 10:
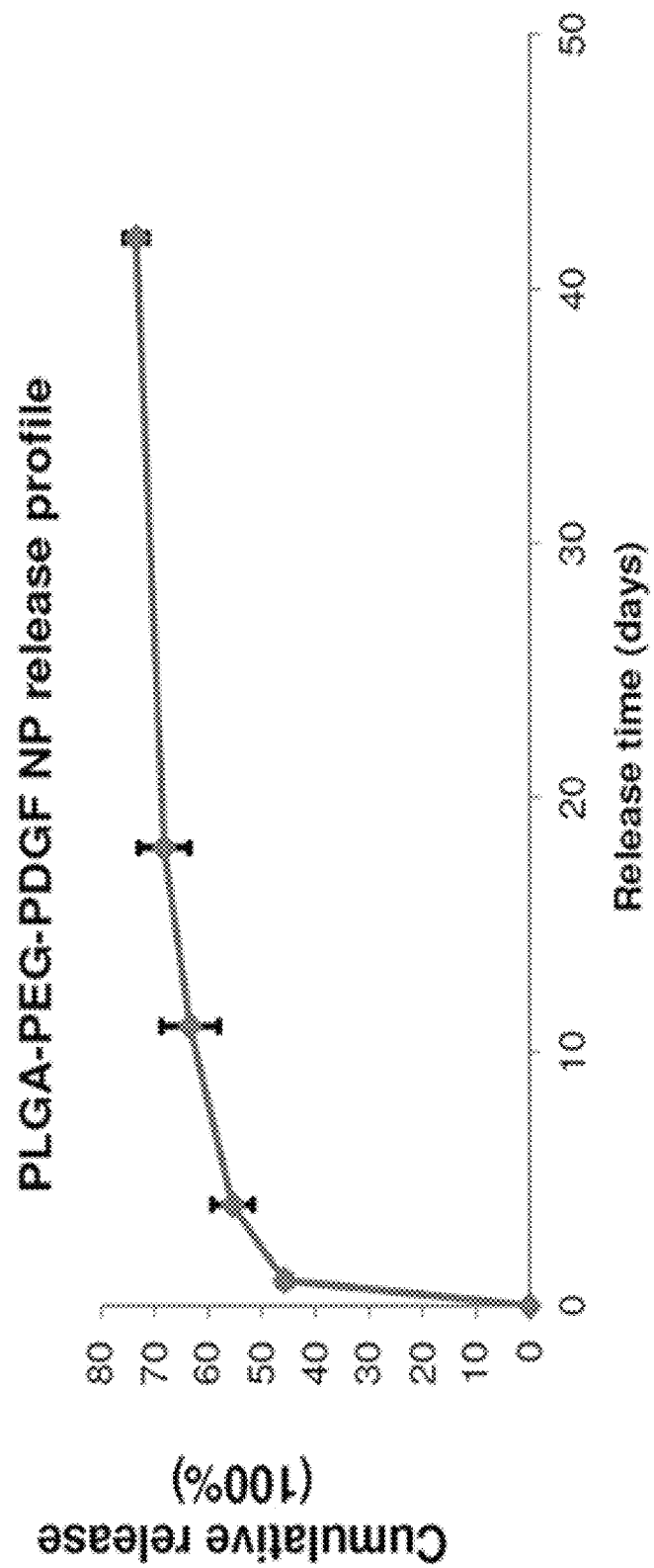
FIG. 10 illustrates the release of platelet derived growth factor from PLGA-m-PEG nanoparticles.

Particle Characterization:

A scanning electron microscope image of the particles, illustrated in FIG. 8, was taken at 5,000× magnification. FIG. 9 is a graph of particle effective diameter versus the percentage of sample, illustrating the particle size distribution. FIG. 10 illustrates the drug release profile of PLGA-m-PEG-PDGF nanoparticles.

Example 3

Formation of Collagen-Nanoparticles Fiber Using the Electrochemical Process

Preparation Method:

Collagen (8.2 mg/mL, soluble collagen extracted from fetal bovine hide) from Collagen Solutions LLC (San Jose, Calif.) was dialyzed at 5° C. for 48 hours to remove the acid (MwCutoff of dialysis tubing, 3500 Da, Spectrum Laboratories, CA). PLGA-based nanoparticles (3 mg/mL) were mixed with dialyzed collagen (3 mg/mL) at a 1:1 ratio and the mixture was loaded inside an electrochemical cell to form aligned nanoparticle-collagen fiber. These multifunctional collagen fibers are able to have a sustained release of PDGF over time to promote tendon repair. The voltage between the two electrodes in the electrochemical cell was 3 volts, which was applied for 30 minutes, with a distance between electrodes of 1.5 mm.

Figure 11A:
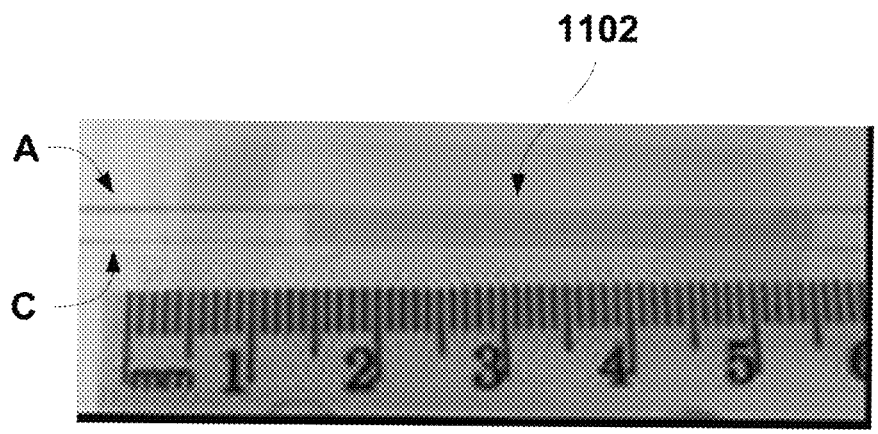
FIG. 11a illustrates a mixture of collagen and nanoparticles provided in an electrochemical cell.
Figure 11B:
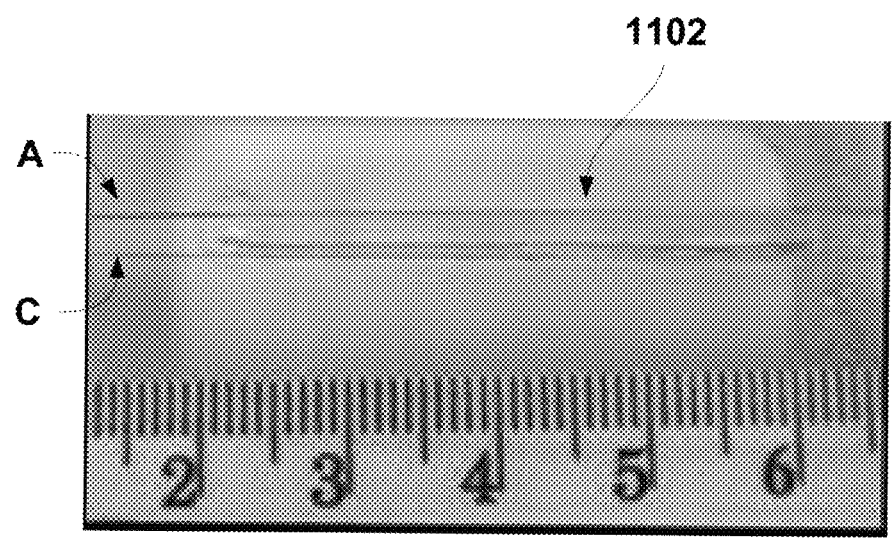
FIG. 11b illustrates an aligned collagen fiber, or wire, produced in the electrochemical cell of FIG. 11b.
Figure 11C:
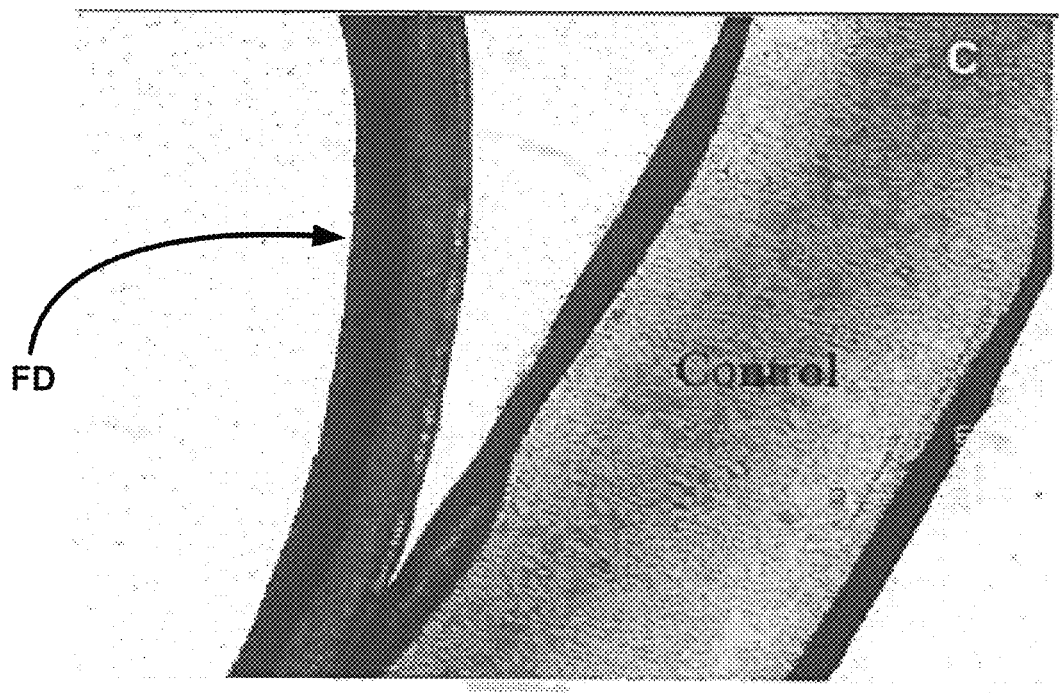
FIG. 11c illustrates an optical micrograph image of aligned collagen fibers produced using the electrochemical cell, wherein one fiber is loaded with a fluorescent dye.
Figure 11D:
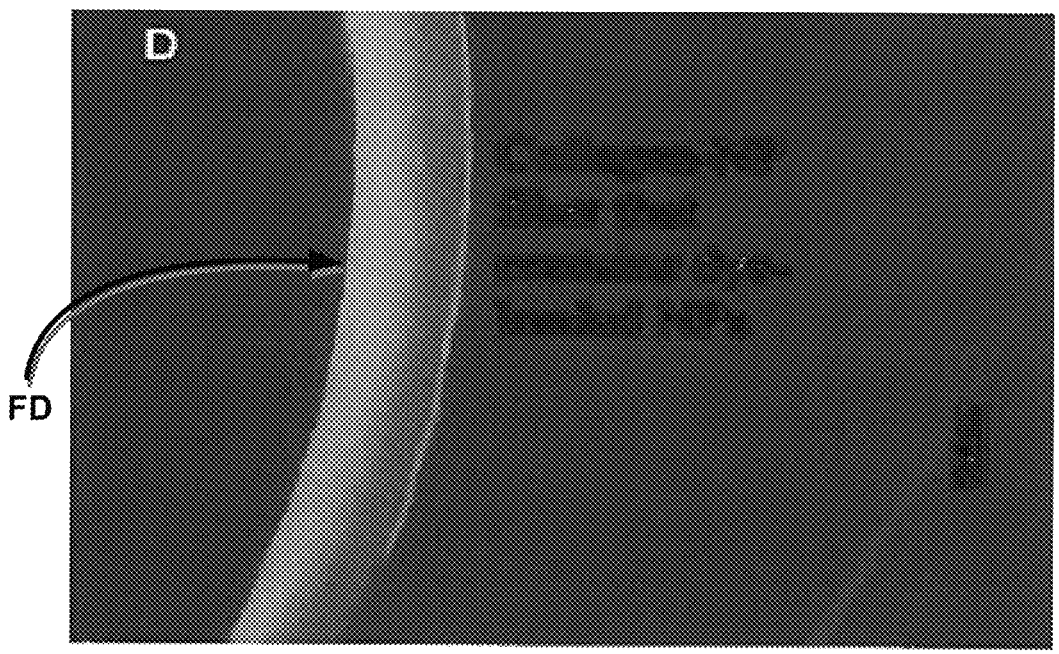
FIG. 11d illustrates a fluorescence optical micrograph image of the aligned collagen fibers of FIG. 11c.

Results:

To visualize the nanoparticle-collagen fiber formation process, the PLGA-m-PEG nanoparticles were prepared using the method outlined above in Example 2, encapsulating Rhodamine 6G fluorescence dye. Initially (T=0), as shown in FIG. 11a, the nanoparticle-collagen mixture 1102 appeared uniformly red inside the cell between two electrodes, anode (A) and cathode (C). After 15 min (T=15 min.), a red nanoparticle-collagen fiber formed close to the cathode side as illustrated in FIG. 11b. FIG. 11c illustrates an optical image of two aligned collagen-nanoparticle containing fibers, wherein one fiber is loaded with the dye (FD). FIG. 11d is the corresponding fluorescence image of FIG. 11c, which confirmed the loading of nanoparticles inside the collagen fiber.

Example 4

Formation of Collagen-Nanoparticle Sheet/Fiber by Using the Electrochemical process Preparation Method:

PLGA-based nanoparticles (3 mg/mL) were mixed with dialyzed collagen (8.2 mg/mL) at a 1:1 ratio following the above described method illustrated in FIG. 3. The mixture was loaded inside the electrochemical chamber to form nanoparticle-collagen sheet as illustrated in FIG. 5. The sheet forming chamber is similar in concept to the fiber formation, with modifications to contain a larger volume of solution. The electrodes in this case are flattened sheets of conductive metal instead of wires.

Figure 12:
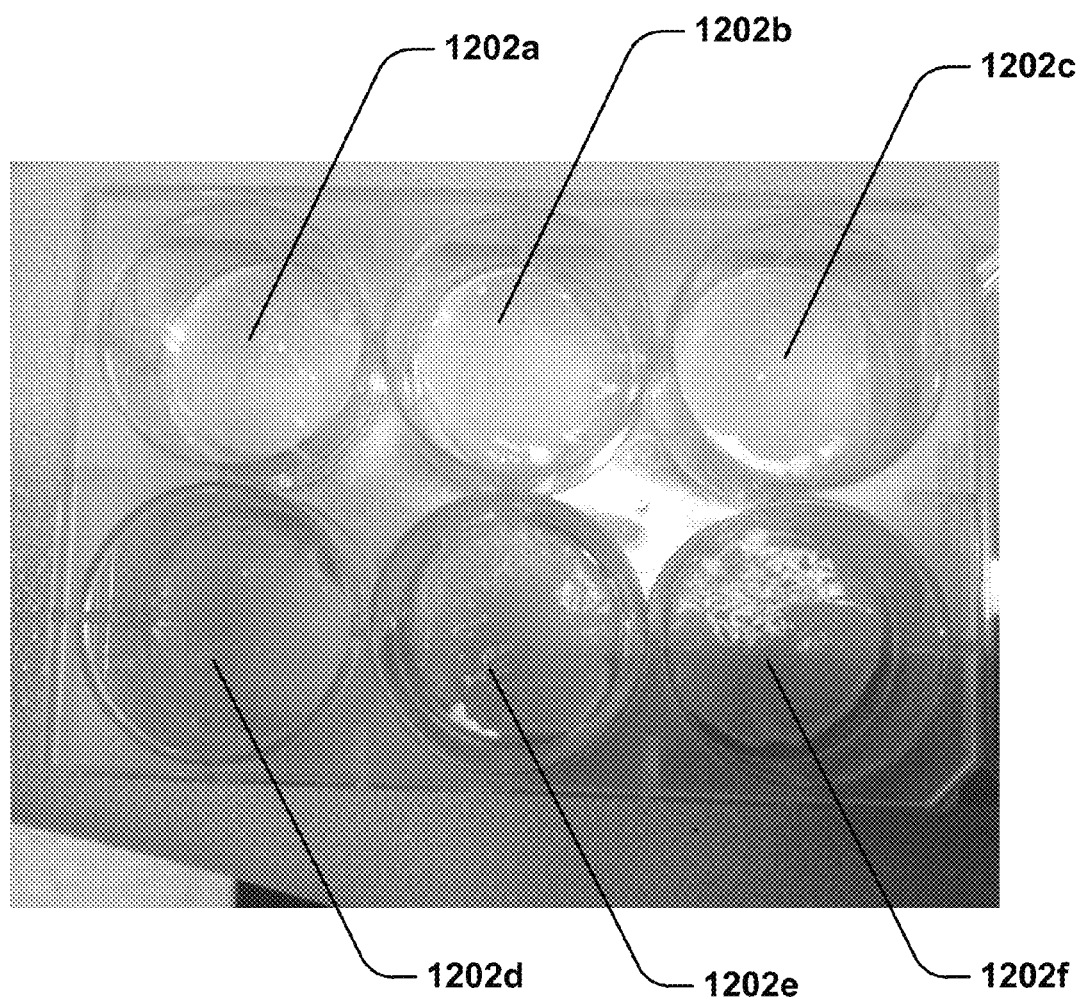
FIG. 12 illustrates an optical micrograph image of collagen sheets in a 6-well cell for culture.
Figure 13:
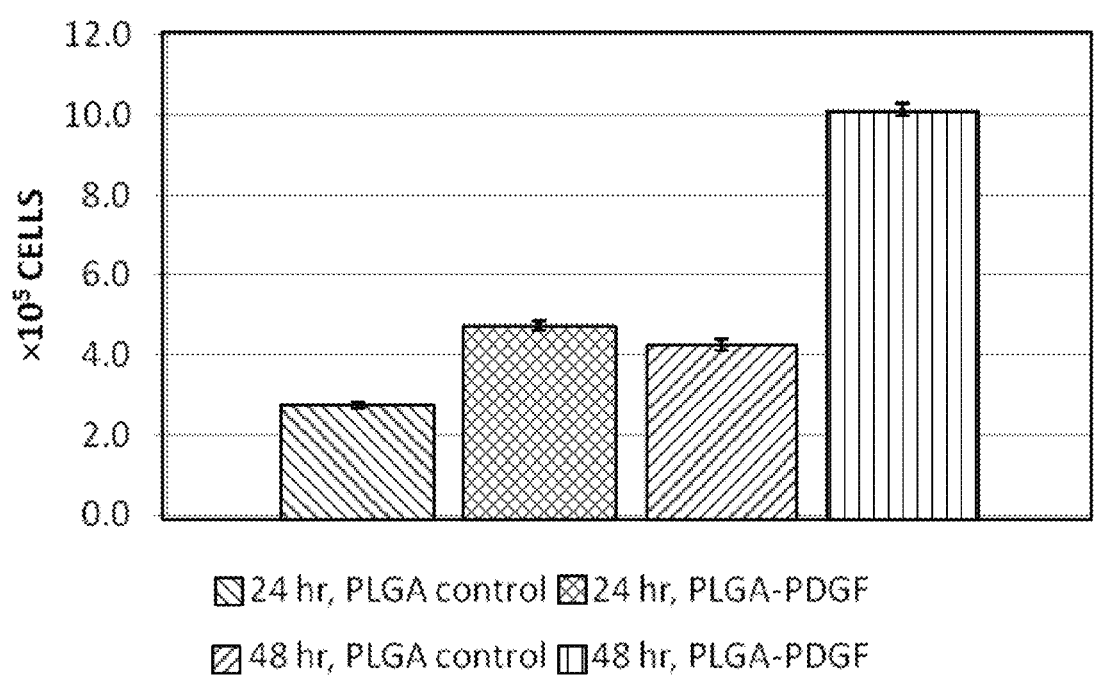
FIG. 13 illustrates the difference in cell proliferation between control PLGA-m-PEG nanoparticles and PLGA-m-PEG nanoparticles encapsulating PDGF.

The collagen-nanoparticle mixture is isoelectrically focused to the cathode surface within the electrochemical chamber. FIG. 12 illustrates formed homogenous collagen sheets 1202a-f, which have been transferred into a 6 well plate for cell culture. The thickness of the sheet can be altered by varying the collagen-nanoparticle solution concentration. The proliferation of adipose-derived stem cells was measured after 24 hour and 48 hour incubation periods. FIG. 13 illustrates preliminary data that shows the collagen/PLGA-m-PEG PDGF nanoparticle sheets (PLGA-PDGF) have an increase, by at least two fold, in adipose-derived stem cells proliferation when compared to a pure collagen sheet (PLGA control). This indicates a controlled release of PDGF from the nanoparticles in suspension.

Figure 14:
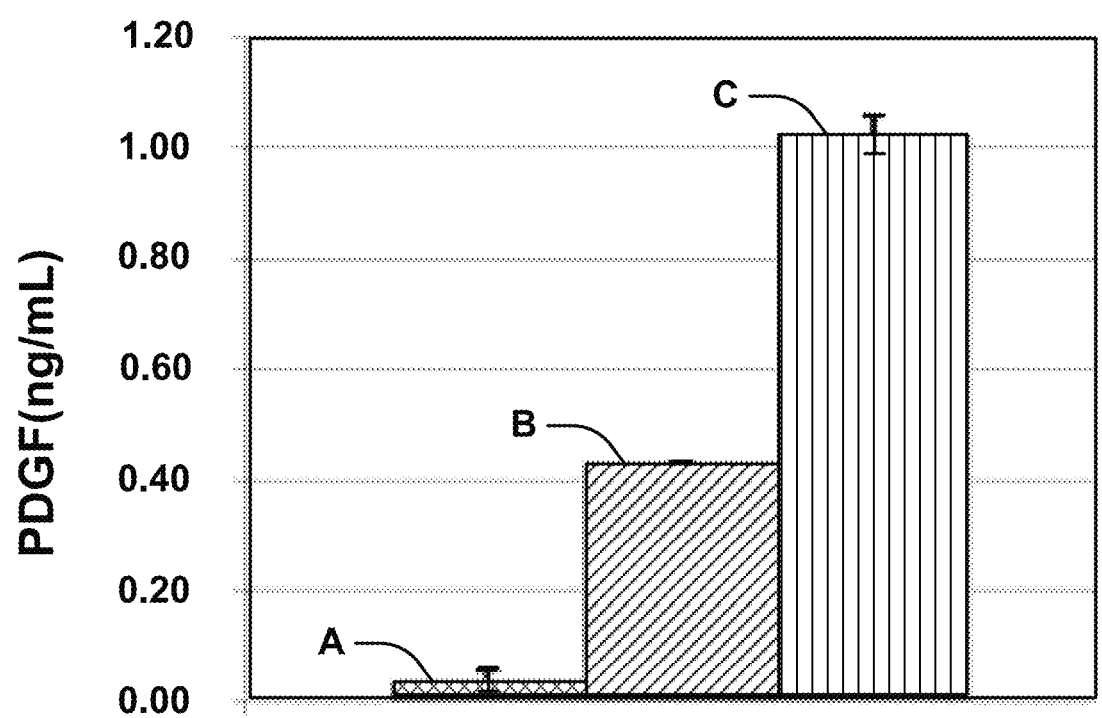
FIG. 14 illustrates the difference in the release of PDGF from aligned collagen fibers including (A) PLGA-m-PEG nanoparticles, (B) DMPC nanoparticles and (C) DMPC nanoparticles lysed with Triton X-100.

Drug Release from Aligned Collagen/Nanoparticle Fibers:

2 mg of dried aligned collagen/PLGA nanoparticle fibers (non-crosslinked) as prepared herein according to Example 3, were digested in 2 mL of 1 mg/mL of collagenase (Type I, Worthington, Inc.) digest solution (50 mM TES, 0.36 mM $CaCl_2$, pH 7.4). The fibers were digested for 48 hrs at 37° C. Similar digestion procedures were used for PDGF release from aligned collagen/DMPC liposome PDGF nanoparticle fibers, wherein the DMPC liposome PDGF nanoparticles were prepared as according to Example 2 and the fibers were prepared in a similar manner to Example 3. For liposome/collagen fibers, the addition of 5% Triton X-100 after collagenase digestion led to total liposome lysis; thus, releasing all PDGF. The PDGF concentration resulting from the digested fibers was measured by a human PDGF-BB ELISA assay (R&D systems, MN). FIG. 14 illustrates the amount of PDGF released from the aligned/PLGA nanoparticle fibers (A), the aligned collagen/DMPC liposome PDGF nanoparticle fibers (B) and the aligned collagen/DMPC liposome PDGF nanoparticle fibers lysed with Triton X-100.

Example 5

Enhancement of Adipose-Derived Cell Proliferation from PLGA-m-PEG Nanoparticle-Collagen Material Preparation Method:

PLGA-m-PEG nanoparticles were encapsulated with PDGF and dialyzed together with acidified collagen following the method above (FIG. 3). This solution was made into aligned fibers using the electrochemical process illustrated above in FIG. 4. Fibers were placed into 6 well culture plates and seeded with adipose derived stem cells (20,000 cells/well).

Figure 15:
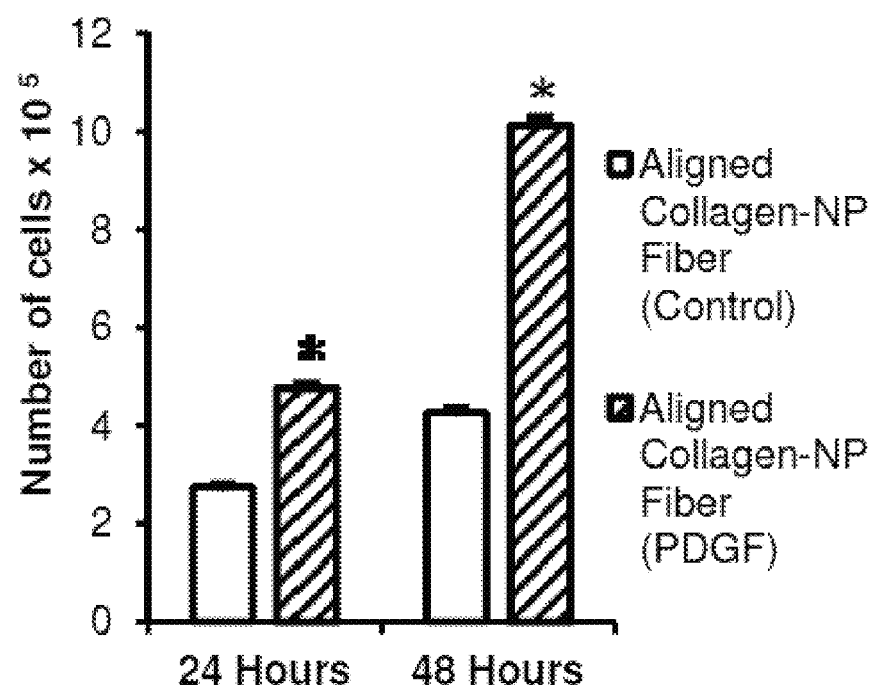
FIG. 15 illustrates the difference in cell proliferation between aligned collagen fibers including control nanoparticles and aligned collagen fibers including nanoparticles encapsulating PDGF.
Figure 16:
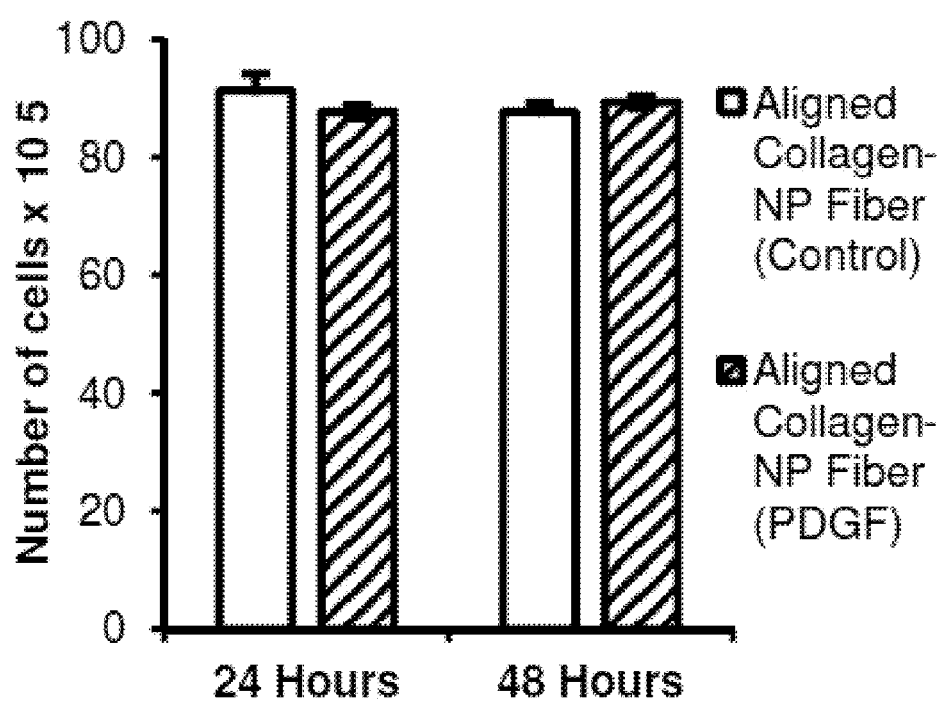
FIG. 16 illustrates the difference in cell viability between aligned collagen fibers including control nanoparticles and aligned collagen fibers including nanoparticles encapsulating PDGF.

Proliferation and Viability:

Adipose derived stem cell proliferation and viability assays were performed on three samples after a 24 hour and 48 hour incubation period. FIG. 15 illustrates the proliferation of cells after the respective incubation periods in the aligned collagen fibers with and without PDGF. FIG. 16 illustrates the proliferation of viability on collagen fiber substrates.

The results indicate that at both 24 and 48 hours after seeding, there is an increase in cell proliferation in the aligned PDGF nanoparticle fibers when compared to aligned control nanoparticle fibers. The number of cells at both time points in the PDGF nanoparticle groups show more than a two fold increase in cell proliferation. This indicates the controlled release of PDGF from the nanoparticles, which in turn activated cell proliferation pathways. As expected, the cell viability of both groups at 24 and 48 hours did not change significantly, proving the biocompatibility of the collagen-nanoparticle substrate.

Example 6

Enhancement of Adipose-Derived Stem Cell Proliferation from Liposome Nanoparticle-Collagen Material Preparation Method and Testing:

Collagen-Liposome nanoparticle sheet were placed inside 6 well cell culture plates (N=3 per well). In the control group, the nanoparticles are not PDGF loaded. In the experiment group, nanoparticles were loaded with PDGF. Adiposed derived stem cells (ADSCs) were seeded in each well at a density of 20,000 cells per well. Plates were incubated at 37° C. at 5% $CO_2$ in serum-free media for either 24 or 48 hours. At designated time points, ADSCs were removed from the plate using 750 µL of 0.25% Trypsin-EDTA for 5 minutes, followed by the addition of 2 mL media. Samples were centrifuged at 4500 rpm for 5 minutes, the supernatant removed and the pellet re-suspended in 500 µL of Mesen-Pro® media.

Figure 17:
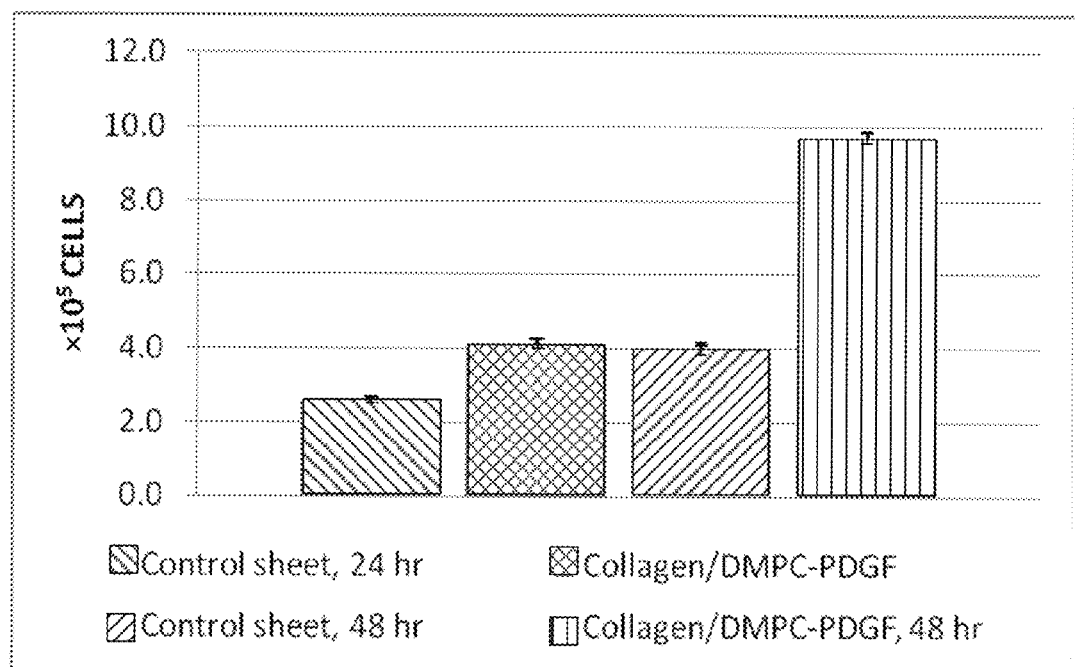
FIG. 17 illustrates the difference in cell proliferation between aligned collagen fibers with and without PDGF encapsulated in the nanoparticles.

After light vortexing, 10 µL of cell suspension was added to 10 µL Trypan Blue and the mixture placed into a cell counting slide. A Countess Automated Cell Counter displayed cell number and viability data. As illustrated in FIG. 17, the results indicate that liposome nanoparticle-collagen sheet loaded with PDGF significantly enhanced the proliferation of ADSCs at both 24 hr and 48 hr as compared to collagen/DMPC sheets without PDGF.

Example 7

Figure 18:
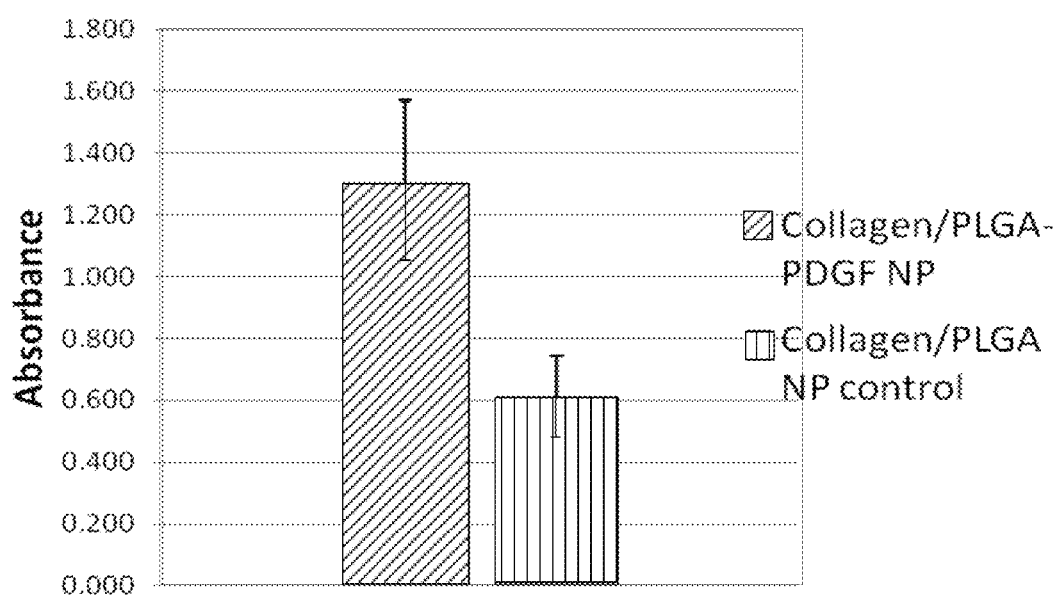
FIG. 18 illustrates the difference between the proliferation of human gingival cells seeded on aligned collagen with and without PDGF encapsulated in the nanoparticles.

Enhancement of Human Gingival Cell Proliferation from PLGA-m-PEG Nanoparticle-Collagen Material Preparation Method and Testing:

Collagen/PLGA nanoparticle sheets were prepared using the method described in FIG. 2. Both groups (control without PDGF and PDGF loaded nanoparticle's) were seeded with $3.8 \times 10^4$ cells and incubated overnight at 37° C. in 5% $CO_2$. The growth media was replaced with serum-free DMEM to establish a baseline to accurately measure the bioactivity of PDGF-BB without it being masked by growth factors found in serum. 3 mL of serum-free (SF) DMEM with antibiotics was used per well. After incubation for 48 hours, the cell proliferation was assayed by WST-1 reagent (Clontech #630118). The higher is the cell number, the higher is the absorbance at 450 nm. The results, as illustrated in FIG. 18, indicate that human gingival cells proliferation was greatly enhanced due to PDGF release from the collagen/PGA-PDGF nanoparticle sheet.

Example 8

Promotion of Adipose-Derived Stem Cell Differentiation into Tendon Fibroblast Lineage Using PLGA-m-PEG Nanoparticle/Collagen Material Preparation Method and Testing:

Aligned fibers were prepared with a PLGA-m-PEG-PDGF nanoparticle-collagen solution following the method mentioned above (FIG. 2) in Example 5. The control aligned fibers contained PLGA-m-PEG-water nanoparticles. Random collagen fibers were prepared using neutralized collagen allowed to gel at 37° C. Amounts of PDGF equal to the aligned PDGF group were added to another group of neutralized collagen and again allowed to gel.

Figure 19:
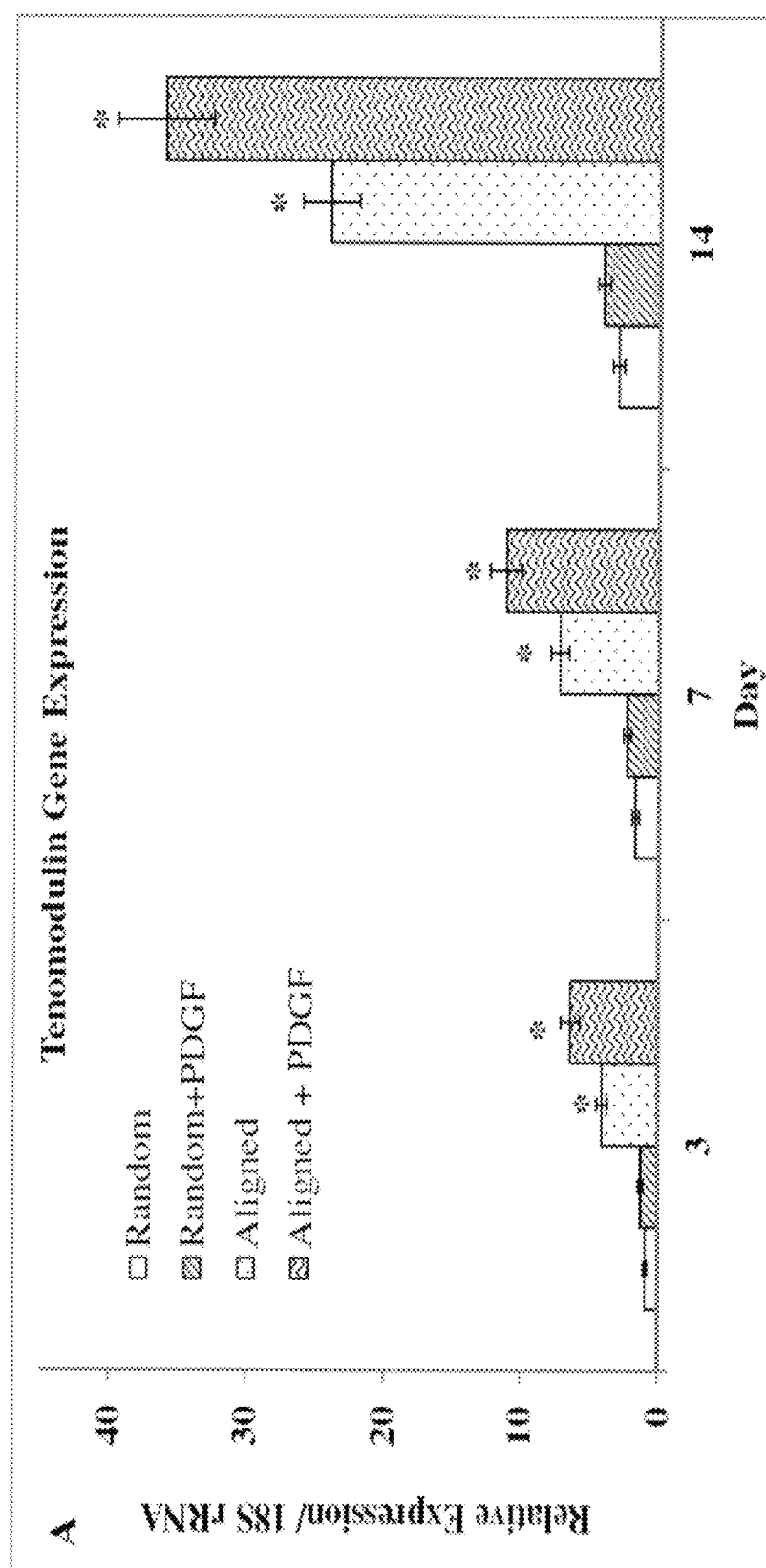
FIG. 19 illustrates the difference in tenomodulin gene expression between random collagen sheets, random collagen sheets including PDGF encapsulated in nanoparticles, aligned collagen sheets and aligned collagen sheets including PDGF encapsulated in the nanoparticles.
Figure 20:
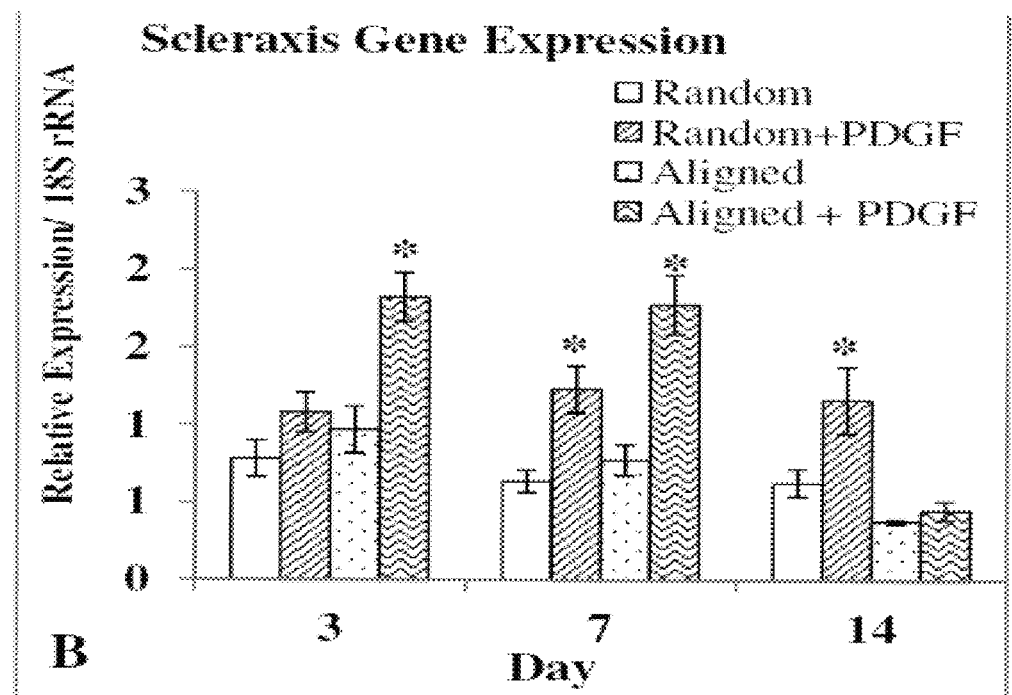
FIG. 20 illustrates the difference in scleraxis gene expression between random collagen sheets, random collagen sheets including PDGF encapsulated in nanoparticles, aligned collagen sheets and aligned collagen sheets including PDGF encapsulated in the nanoparticles.
Figure 21:
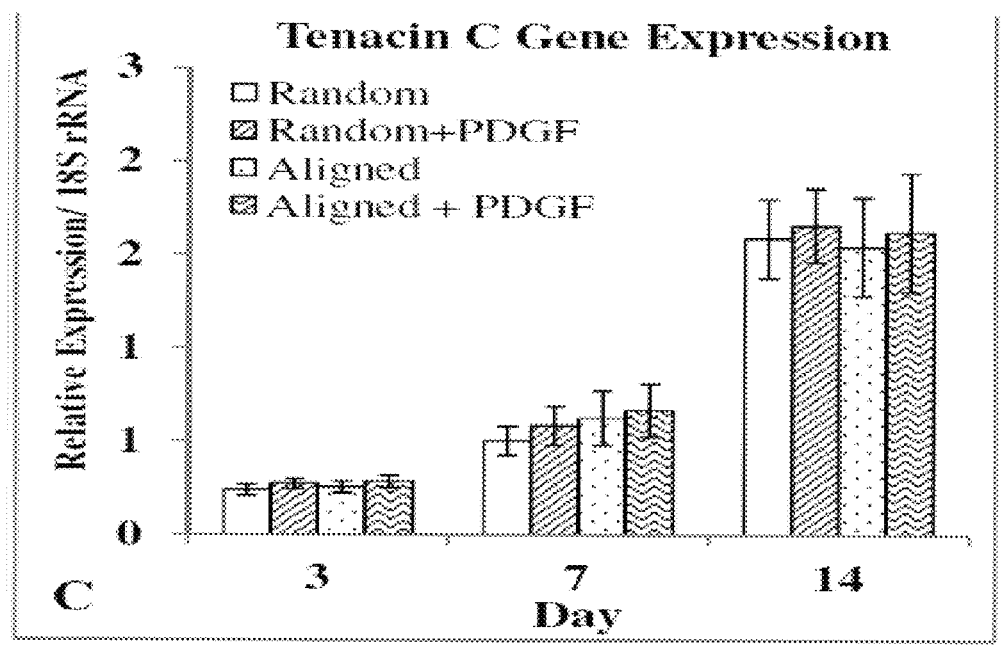
FIG. 21 illustrates the difference in tenascin C gene expression between random collagen sheets, random collagen sheets including PDGF encapsulated in nanoparticles, aligned collagen sheets and aligned collagen sheets including PDGF encapsulated in the nanoparticles.

Tenomodulin (TNMN; Tenocyte Marker), Scleraxis, and Tenascin C Expression:

The expression of key genes (TNMD, SCXA/SCXB, TNC) was measured in the aligned collagen fiber with the PDGF encapsulated nanoparticles using real time-PCR at 3, 7 and 14 days after seeding with stem cells. The results show a significant increase in the TNMN gene in the aligned collagen fiber with PDGF encapsulated nanoparticles. Specifically, reference is made to FIG. 19, which illustrates the increase in tenomodulin gene expression in random and aligned collagen fiber with PDGF encapsulated nanoparticles as compared to the random and aligned collagen fibers without PDGF, respectively. Furthermore, the aligned PDGF exhibits an increased tenomodulin gene expression as compared to the random fibers including PDGF. There was also a significant decrease of scleraxis expression in samples including aligned collagen fibers with PDGF when compared to other group as illustrated in FIG. 20. Tenascin C did not have any significant difference between the groups but it increased over time across all groups as illustrated in FIG. 21. These results indicate that the collagen/PDGF nanoparticle aligned fiber is conducive to the differentiation of adipose-derived stem cells to tenocyte lineage.

Example 9

Biomechanical Testing of Stem Cell Seeded Aligned Collagen-Nanoparticle Constructs Preparation Method:

Aligned collagen-nanoparticle composite fibers were prepared as described above in Example 3. In addition, random collagen fibers were created by heat gelation at 37° C. using dialyzed collagen solution supplemented with 10× PBS and inserting it into a mold. After the fibers were dry, a small amount of soluble PDGF with same overall nominal loading as aligned collagen-NP fiber (50 ng/fiber) was loaded inside for the PDGF group. The fibers were seeded with adipose-derived stem cells. After twenty one days from seeding, the aligned and random collagen fibers were dehydrated.

Tensile Testing:

The dehydrated fibers were tensile tested to determine their tensile mechanical properties. Both ends of dried bundles were fixed between thin PVC tabs using cyanoacrylate and the bundles were rehydrated in phosphate-buffered saline. Prior to testing, rehydrated specimen thickness was measured using a calibrated digital microscope (VHX-100, Keyence Corp., Elmwood Park, N.J.). Substantial variation in with was observed along the length of each specimen. In order to accurately determine initial specimen width, photographic images of the specimens were collected by digital microscope (prior to testing) in order to allow initial specimen width to be determine at the approximate point of specimen failure following tensile testing.

Specimens were mounted in a moving magnet linear motor testing frame (Electroforce 3330, Bose Corporation, Eden Prairie, Minn.), and loaded monotonically under displacement control (10 mm/min) to tensile failure. Crosshead displacement was measured using the testing frame LVDT and load was measured using a 5 lb (22.24 N) load cell (Transducer Techniques, Temecula, Calif.). A total of 6 random collagen fibers and 7 aligned collagen-NP fibers were tested. After testing, specimen width was determined from the calibrated photographs obtained prior to the testing at the approximate point of failure. Initial specimen length was determined based on detection of a non-zero tensile load. Specimen strain was determined by dividing displacement data by initial specimen length and stress was determined by dividing load data by the cross-sectional area calculated as the project of specimen thickness and width at the point of failure. The elastic region was identified within the stress strain data by using a moving window approach (minimum window size of 0.45 seconds=45 data points) to detect any reduction in the slope of the stress-strain data within the elastic region. Peak tensile stress and strain at the point of peak tensile stress were also determined.

Figure 22:
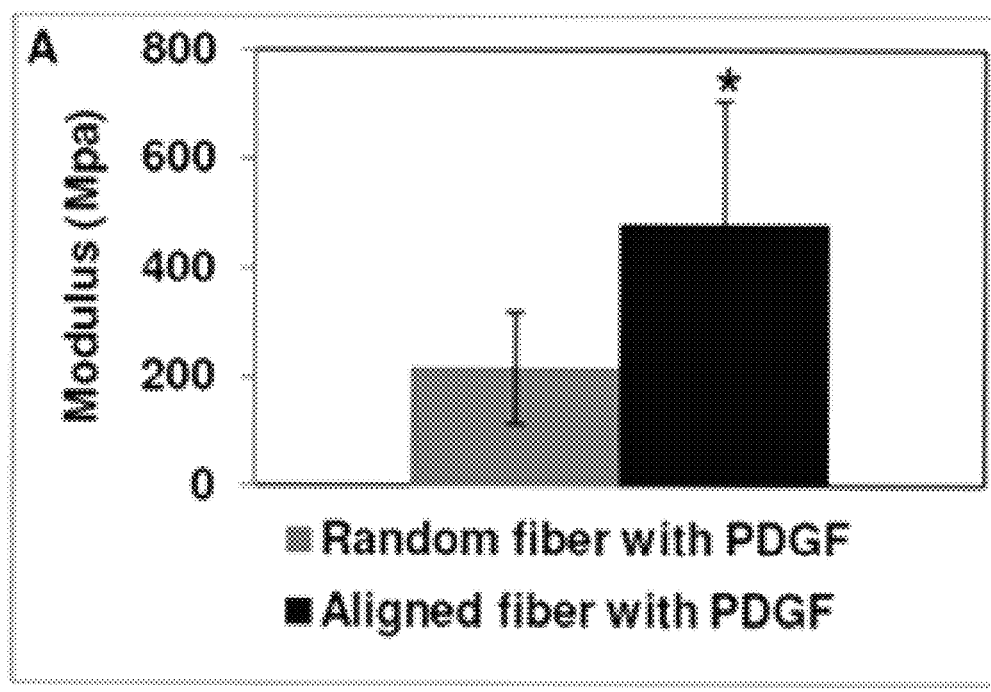
FIG. 22 illustrates an example of the modulus of random collagen fiber including PDGF versus the modulus of aligned collagen fiber with PDGF.
Figure 23:
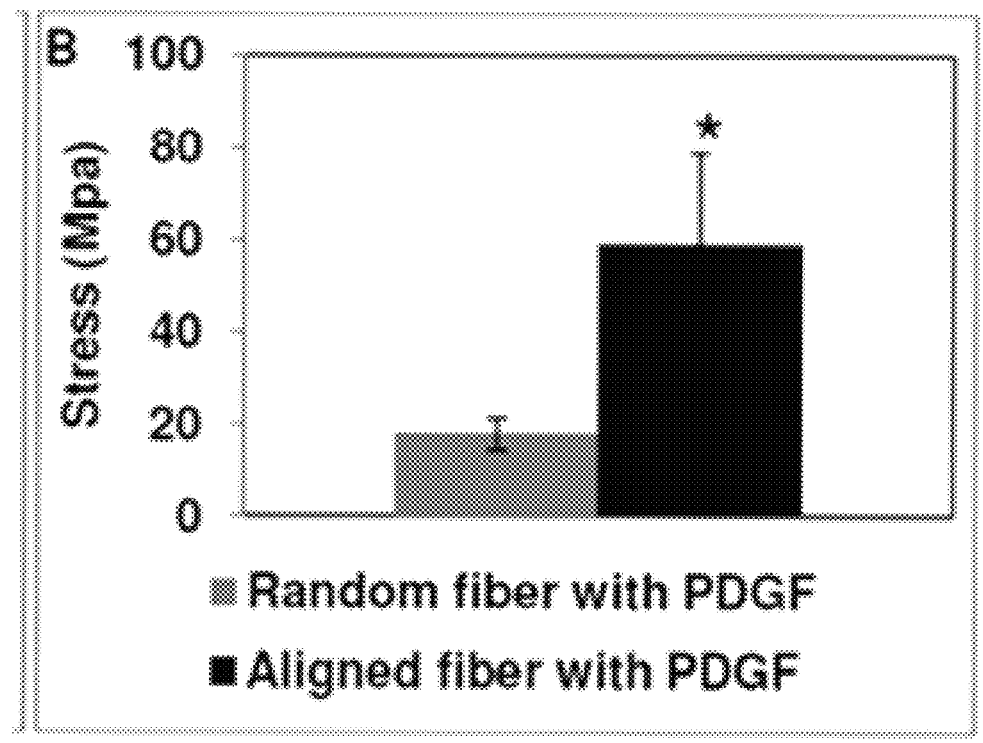
FIG. 23 illustrates the stress of random collagen fiber including PDGF versus the modulus of aligned collagen fiber with PDGF.

As illustrated in FIGS. 22 and 23, the PDGF-releasing aligned collagen-NP fiber has relatively higher modulus ($P<0.05$, FIG. 22) and relatively higher peak stress ($P<0.05$, see FIG. 23) compared to random collagen fibers which contain PDGF.

Example 10

Formation of 3D Aligned Collagen-Nanoparticle Fiber Scaffolds for Implantation

Preparation Method:

Unwashed PLGA-m-PEG-PDGF nanoparticles suspended in 1% sodium cholate were prepared according to Example 2. This solution was dialyzed for 48 hours in MWCO3500 dialysis bags refreshing the water every 2-3 hours. PDGF nanoparticles were mixed with dialyzed collagen (8.2 mg/mL Collagen Solutions LLC, CA) at a 1:1 ratio. The collagen-nanoparticle-free PDGF solution was then used to create aligned fibers by loading the solution into an electrochemical chamber and a voltage was applied to create the aligned fiber. The electrochemical chamber consisted of two platinum electrodes spaces 1.5 mm apart from each other. A DC voltage of 3.0 volts was applied across the electrochemical gradient, and the fiber was collected near the cathode side of the chamber after 30 minutes. Fibers collected were then either air dried on PARAFILM sheets for later use or placed into a 1% 1-ethyl-3-(3-dimethylaminopropyl)carbondiimide (EDC) (Thermoscientific, IL) crosslinking solution immediately after forming, and left for 24 hours at room temperature. After crosslinking, the fibers were washed thoroughly with e-pure water, and then air dried on PARAFILM sheet for later use.

A total of ten fibers were used to create one aligned collagen scaffolds. The fibers were prepared as described above. Eight fibers were EDC cross-linked while the remaining two were directly dehydrated. In order to prepare a braided scaffold design to further enhance tensile strength, the ten fibers were divided into three groups, and braided together using a standard braid within those three groups. The three bundles of braided fibers were again braided together using a standard braid complex of ten total fibers.

Figure 24A:
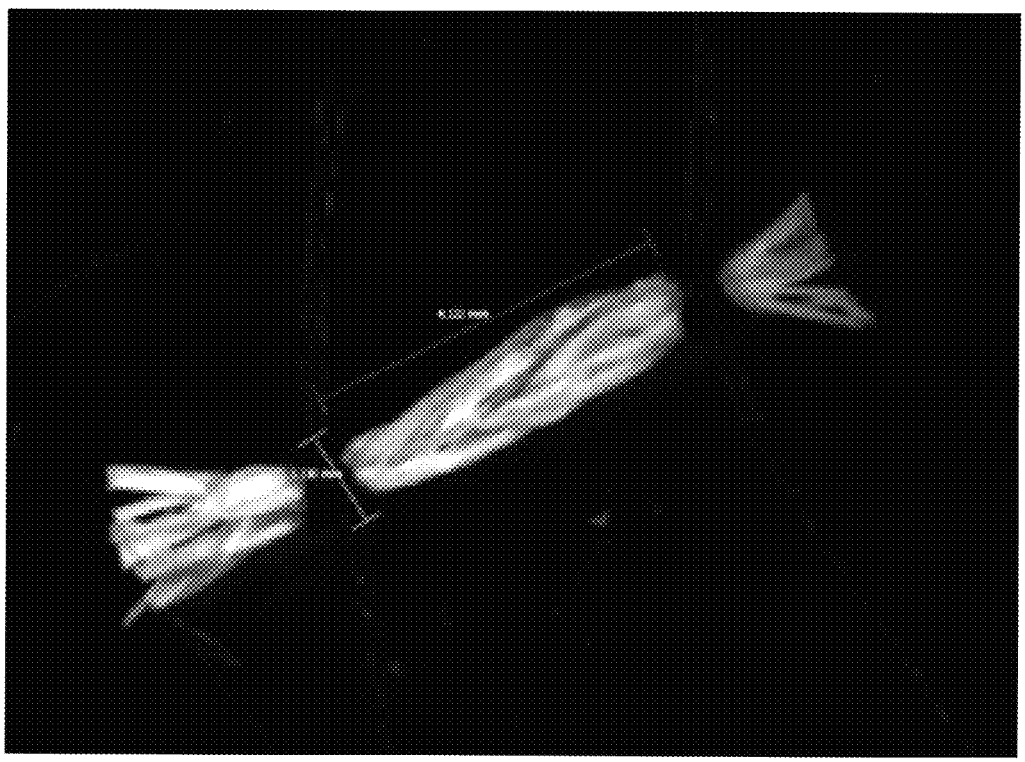
FIG. 24a illustrates an optical micrograph of a collagen fiber construct at 10× magnification.
Figure 24B:
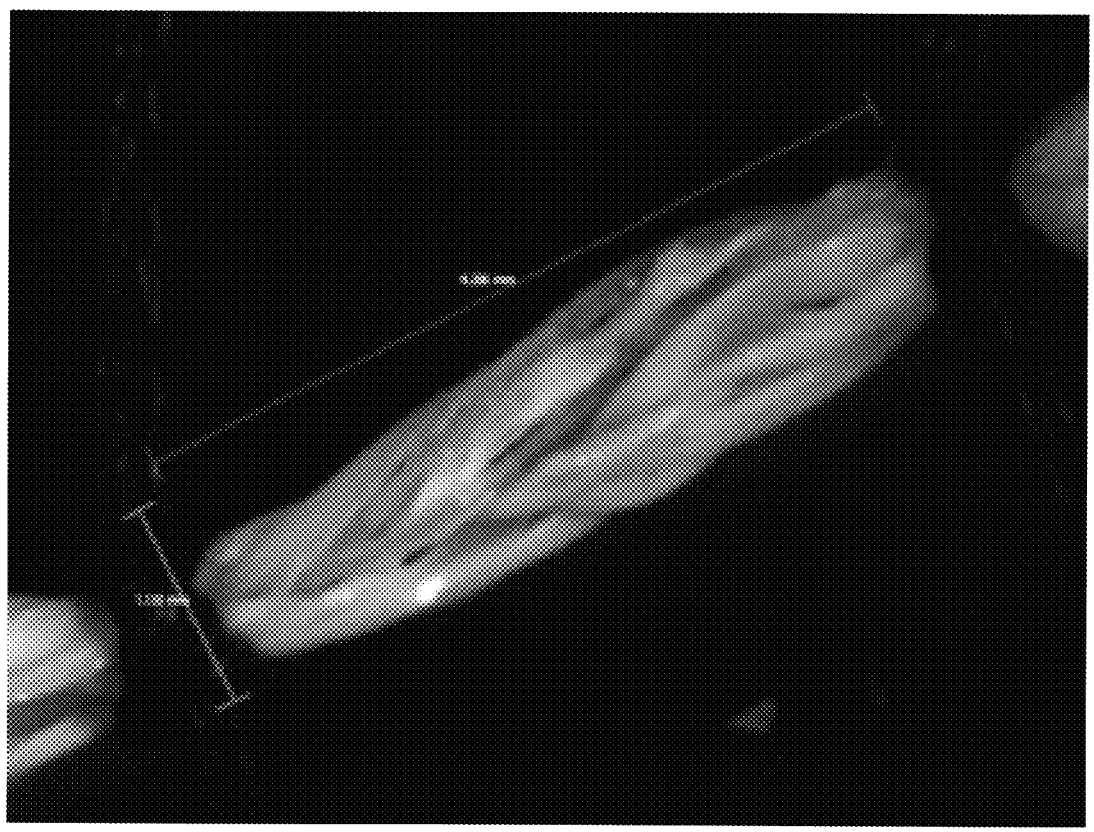
FIG. 24b illustrates an optical micrograph of a collagen fiber construct at 20× magnification.

The ends of the braids were secured using 4-0 PERMA-HAND silk sutures (Ethicon, Tex.) tied with a surgical constriction know. Scaffolds were made to be 3.0-5.0 mm in length in between silk sutures. FIGS. 24a and 24b illustrate an example of a scaffold at 10× and 20× magnification.

Figure 25A:
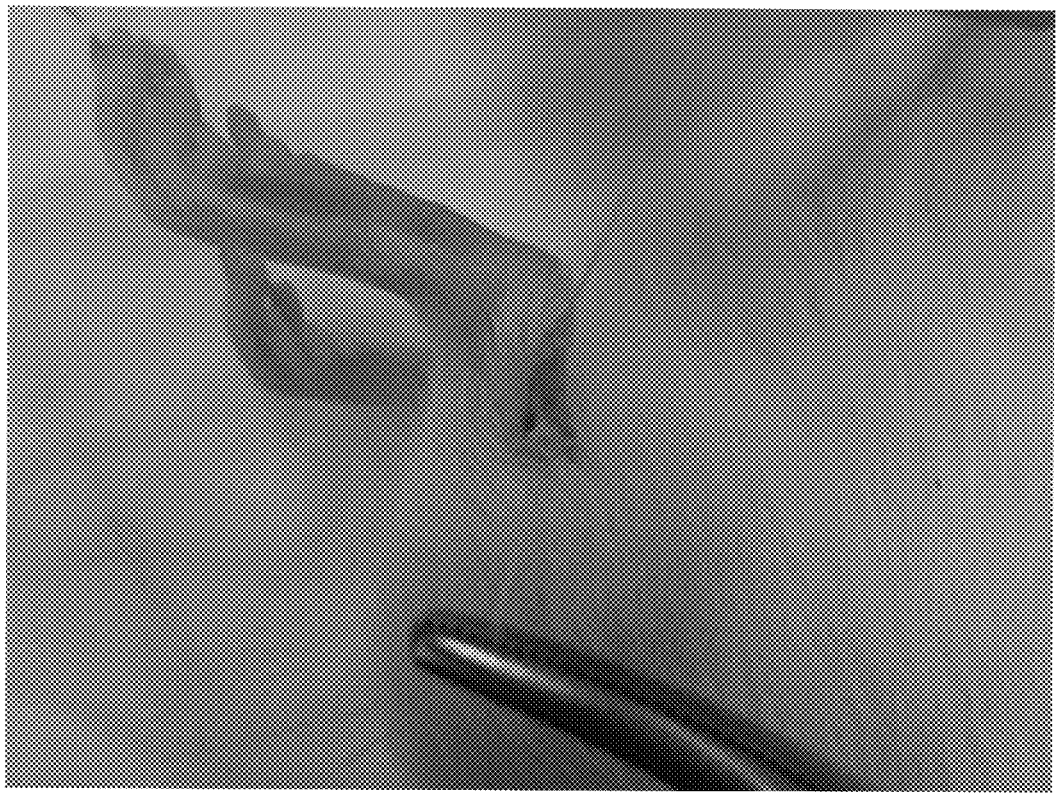
FIG. 25a illustrates the suturing of a scaffold to a severed Achilles tendon gap defect.
Figure 25B:
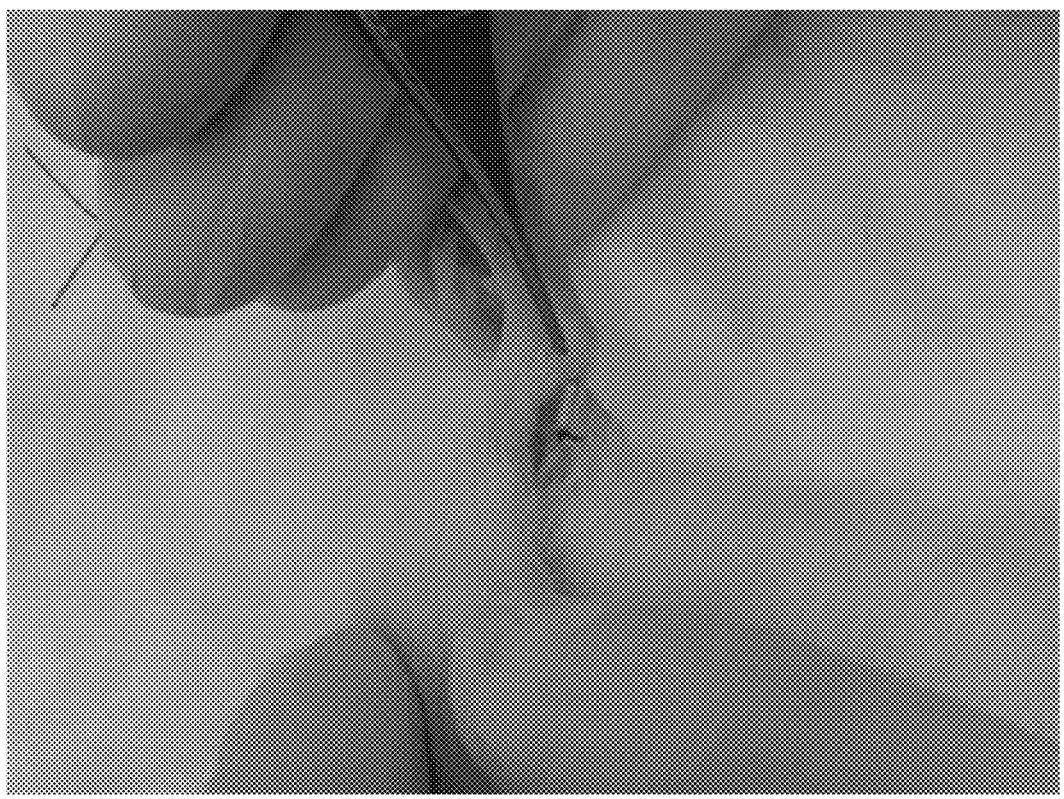
FIG. 25b illustrates a scaffold in place in the defect site of the Achilles tendon.

Scaffold Testing:

Using 6-0 suture and interrupted stiches the collagen scaffolds were secured between two ends of a severed Achilles tendon, spanning the gap of the segment removed. FIG. 25a illustrates suturing of the scaffold into a severed Achilles tendon gap defect in a rat and FIG. 25b illustrates a scaffold in place at the defect site. The scaffold held in place well and upon flexation of the foot, the repaired tendon stretched and the scaffold did not break or come loose. Braided construct, when sutured to tendon ends properly, appeared to perform as a robust synthetic graft. This data suggests that 3-D aligned collagen-NP fiber scaffolds can be implanted for tendon/ligament, or nerve repair regeneration applications.

While representative and preferred embodiments of the present invention have been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadened scope of the invention which the Applicant is entitled to claim, or the only manner(s) in which the invention may be claimed, or that all recited features are necessary.

What is claimed is:

1. A method of forming an article, comprising:
mixing a polymer in solution with nanoparticles to form a polymer-nanoparticle mixture, wherein said nanoparticles exhibit an effective diameter in the range of 1 nm to 300 nm and encapsulate a pharmaceutical composition including a growth factor, bovine serum albumin or combinations thereof;
placing said mixture in an electrochemical cell;
contacting said mixture with at least one electrode;
applying a voltage in the range of 1 V to 30 V to said electrochemical cell and generating a pH gradient in the range of 3.0 to 11.0;
aligning said polymer at the isoelectric point of the polymer in solution; and
forming an article of aligned polymer including said nanoparticles without covalently bonding said nanoparticles to said polymer, wherein said nanoparticles exhibit polar interactions between the nanoparticles and the aligned polymer and said nanoparticles are loaded into said polymer in an amount of at least 25 wt % and said aligned polymer exhibits a modulus in the range of 50 MPa to 1.5 GPa, a tensile stress in the range of 0.5 MPa to 150 MPa, and a tensile strain in the range of 0.05% to 30%, wherein said modulus, tensile stress and tensile strain are obtained at a testing rate of 10 mm/min and using a 22.24 N load cell.

2. The method of claim 1, wherein said polymer is collagen.

3. The method of claim 1, wherein said nanoparticles encapsulate an additional pharmaceutical composition.

4. The method of claim 3, wherein said pharmaceutical composition includes a dye.

5. The method of claim 3, wherein said pharmaceutical composition includes platelet derived growth factor.

6. The method of claim 1, wherein said nanoparticles include liposomes.

7. The method of claim 6, wherein said nanoparticles exhibit a polydispersity in the range of 0.050 to 0.300.

8. The method of claim 1, wherein said article exhibits a wall thickness in the range of 100 µm to 2.0 mm.

9. The method of claim 6, wherein said nanoparticles exhibit a loading efficiency in the range of 75% to 95% as determined by Lowry protein assay and enzyme-linked immunosorbent assay.

10. The method of claim 6, wherein said nanoparticles are formed by dissolving phosphocholine in a solvent; evaporating said solvent and forming a cake; hydrating said cake with a solution of said pharmaceutical composition and forming said liposomes; sizing said liposomes; and dialyzing said liposomes.

11. The method of claim 10, wherein said phosphocholine is 1,2-distearoyl-sn-glycero-3-phosphocholine.

12. The method of claim 10, wherein said phosphocholine is 1,2-dimyristoyl-sn-glycero-3-phosphocholine.

13. The method of claim 10, wherein said solution comprises a) platelet derived growth factor in the range of 25 µg/mL to 2 mg/mL, b) said bovine serum albumin in the range of 1 mg/mL to 20 mg/mL, or combinations thereof.

14. The method of claim 10, wherein when said pharmaceutical composition includes platelet derived growth factor said solution comprises water, buffered solutions, or non-electrolyte solutions.

15. The method of claim 3, wherein said nanoparticles comprise poly(lactic-co-glycolic acid)-monomethoxy-poly (ethylene glycol).

16. The method of claim 15, wherein said nanoparticles are formed by dissolving the PLGA-m-PEG in a solvent; adding a pharmaceutical composition in solution to said PLGA-m-PEG in said solvent and emulsifying to form a mixture; adding a surfactant solution to said mixture and emulsifying; and evaporating said solvent.

17. The method of claim 1, wherein said aligned polymer article is formed into a shape selected from the following group consisting of: rectangular, square, circular, tubular, ring and combinations thereof.

18. A method of forming an article, comprising:
mixing a polymer in solution with liposome nanoparticles to form a polymer-nanoparticle mixture, wherein said nanoparticles encapsulate a platelet derived growth factor or bovine serum albumin, and exhibit an effective diameter in the range of 1 nm to 300 nm and a polydispersity in the range of 0.050 to 0.300;
placing said mixture in an electrochemical cell;
contacting said mixture with at least one electrode;
applying a voltage in the range of 1 V to 30 V to said electrochemical cell and generating a pH gradient in the range of 3.0 to 11.0;
aligning said polymer at the isoelectric point of the polymer in solution; and
forming an article of aligned polymer including said nanoparticles without covalently bonding said nanoparticles to said polymer, wherein said nanoparticles exhibit polar interactions between the nanoparticles and the aligned polymer and said nanoparticles are loaded into said polymer in an amount of at least 25 wt % and said aligned polymer exhibits a modulus in the range of 50 MPa to 1.5 GPa, a tensile stress in the range of 0.5 MPa to 150 MPa, and a tensile strain in the range of 0.05% to 30%, wherein said modulus, tensile stress and tensile strain are obtained at a testing rate of 10 mm/min and using a 22.24 N load cell.

\* \* \* \* \*